US012070292B2

(12) United States Patent
Freeman et al.

(10) Patent No.: US 12,070,292 B2
(45) Date of Patent: *Aug. 27, 2024

(54) SYSTEMS AND METHODS OF INTEGRATING AMBULATORY MEDICAL DEVICES

(71) Applicant: ZOLL Medical Corporation, Chelmsford, MA (US)

(72) Inventors: Gary A. Freeman, Waltham, MA (US); Suzanne Crowell, Beverly, MA (US); Shane S. Volpe, Saltsburg, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 100 days.

This patent is subject to a terminal disclaimer.

(21) Appl. No.: 17/869,091

(22) Filed: Jul. 20, 2022

(65) Prior Publication Data
US 2022/0354367 A1 Nov. 10, 2022

Related U.S. Application Data

(63) Continuation of application No. 16/862,752, filed on Apr. 30, 2020, now Pat. No. 11,432,722, which is a
(Continued)

(51) Int. Cl.
*A61B 5/00* (2006.01)
*A61B 5/01* (2006.01)
(Continued)

(52) U.S. Cl.
CPC .............. *A61B 5/0022* (2013.01); *A61B 5/01* (2013.01); *A61B 5/0205* (2013.01);
(Continued)

(58) Field of Classification Search
CPC ....... A61B 5/0022; A61B 5/01; A61B 5/0205; A61B 5/02055; A61B 5/1118;
(Continued)

(56) References Cited

U.S. PATENT DOCUMENTS 3,724,455 A 4/1973 Unger
3,922,665 A 11/1975 Curry et al.
(Continued)

FOREIGN PATENT DOCUMENTS

EP 0707825 4/1996
EP 0761255 3/1997
(Continued)

OTHER PUBLICATIONS

"Medical Electrical Equipment—Part 2-4: Particular Requirements for the Safety of Cardiac Defibrillators (including Automated External Defibrillators)", Association for the Advancement of Medical Instrumentation, 2004, ANSI/AAMI DF80:2003; ISBN 1-57020-210-9; abstract; p. vi, p. 50, section 107.1.2.
(Continued)

*Primary Examiner* — Mark W. Bockelman
(74) *Attorney, Agent, or Firm* — Finch & Maloney PLLC

(57) ABSTRACT

An ambulatory medical device is provided. The ambulatory medical device includes at least one sensor configured to acquire physiological data of a patient, at least one network interface and at least one processor coupled to the at least one sensor and the at least one network interface. The at least one processor is configured to detect, via the at least one network interface, a medical device, to establish a secure communication session with the medical device via the at least one network interface, to detect a data capacity of the secure communication session, to identify a category of patient data associated with the data capacity, and to transmit patient data of the category to the medical device via the secure communication session.

19 Claims, 12 Drawing Sheets

Related U.S. Application Data continuation of application No. 15/472,485, filed on Mar. 29, 2017, now Pat. No. 10,674,911.

(60) Provisional application No. 62/315,486, filed on Mar. 30, 2016.

(51) Int. Cl.

| | | |
|---|---|---|
| *A61B 5/0205* | (2006.01) | |
| *A61B 5/08* | (2006.01) | |
| *A61B 5/11* | (2006.01) | |
| *A61B 5/1455* | (2006.01) | |
| *A61B 5/332* | (2021.01) | |
| *A61B 5/349* | (2021.01) | |
| *A61H 31/00* | (2006.01) | |
| *A61N 1/04* | (2006.01) | |
| *A61N 1/362* | (2006.01) | |
| *A61N 1/39* | (2006.01) | |
| *G16H 40/63* | (2018.01) | |
| *G16H 40/67* | (2018.01) | |
| *G16H 50/20* | (2018.01) | |
| *G16H 50/30* | (2018.01) | |
| *H04W 4/80* | (2018.01) | |
| *H04W 84/12* | (2009.01) | |

(52) U.S. Cl.
CPC ........ *A61B 5/02055* (2013.01); *A61B 5/1118* (2013.01); *A61B 5/14551* (2013.01); *A61B 5/332* (2021.01); *A61B 5/349* (2021.01); *A61B 5/746* (2013.01); *A61H 31/005* (2013.01); *A61H 31/007* (2013.01); *A61N 1/3904* (2017.08); *A61N 1/3925* (2013.01); *G16H 40/63* (2018.01); *G16H 40/67* (2018.01); *G16H 50/20* (2018.01); *G16H 50/30* (2018.01); *A61B 5/08* (2013.01); *A61B 5/6831* (2013.01); *A61H 2201/1253* (2013.01); *A61H 2201/1619* (2013.01); *A61H 2201/165* (2013.01); *A61H 2201/5012* (2013.01); *A61H 2201/5015* (2013.01); *A61H 2201/5084* (2013.01); *A61H 2230/04* (2013.01); *A61H 2230/06* (2013.01); *A61N 1/046* (2013.01); *A61N 1/0484* (2013.01); *A61N 1/3625* (2013.01); *A61N 1/3993* (2013.01); *H04W 4/80* (2018.02); *H04W 84/12* (2013.01)

(58) Field of Classification Search
CPC ..... A61B 5/14551; A61B 5/332; A61B 5/349; A61B 5/746; A61B 5/08; A61B 5/6831; A61H 31/005; A61H 31/007; A61H 2201/1253; A61H 2201/1619; A61H 2201/165; A61H 2201/5012; A61H 2201/5015; A61H 2201/5084; A61H 2230/04; A61H 2230/06; A61N 1/3904; A61N 1/3925; A61N 1/046; A61N 1/0484; A61N 1/3625; A61N 1/3993; G16H 40/63; G16H 40/67; G16H 50/20; G16H 50/30; H04W 4/80; H04W 84/12
See application file for complete search history.

(56) References Cited

U.S. PATENT DOCUMENTS

| | | |
|---|---|---|
| 4,576,170 A | 3/1986 | Bradley et al. |
| 4,580,572 A | 4/1986 | Granek et al. |
| 4,583,547 A | 4/1986 | Granek et al. |
| 4,729,377 A | 3/1988 | Granek et al. |
| 4,928,690 A | 5/1990 | Heilman et al. |
| 4,991,217 A | 2/1991 | Garrett et al. |
| 5,078,134 A | 1/1992 | Heilman et al. |
| 5,348,008 A | 9/1994 | Bornn et al. |
| 5,371,692 A | 12/1994 | Draeger et al. |
| 5,381,798 A | 1/1995 | Burrows |
| 5,741,306 A | 4/1998 | Glegyak et al. |
| 5,929,601 A | 7/1999 | Kaib et al. |
| 5,944,669 A | 8/1999 | Kaib |
| 6,065,154 A | 5/2000 | Hulings et al. |
| 6,097,982 A | 8/2000 | Glegyak et al. |
| 6,141,584 A | 10/2000 | Rockwell et al. |
| 6,148,233 A | 11/2000 | Owen et al. |
| 6,160,964 A | 12/2000 | Imoto |
| 6,253,099 B1 | 6/2001 | Oskin et al. |
| 6,280,461 B1 | 8/2001 | Glegyak et al. |
| 6,304,780 B1 | 10/2001 | Owen et al. |
| 6,336,900 B1 | 1/2002 | Alleckson et al. |
| 6,356,785 B1 | 3/2002 | Snyder et al. |
| 6,374,138 B1 | 4/2002 | Owen et al. |
| 6,390,996 B1 | 5/2002 | Halperin et al. |
| 6,405,083 B1 | 6/2002 | Rockwell et al. |
| 6,406,426 B1 | 6/2002 | Reuss et al. |
| 6,418,346 B1 | 7/2002 | Nelson et al. |
| 6,438,417 B1 | 8/2002 | Rockwell et al. |
| 6,442,433 B1 | 8/2002 | Linberg |
| 6,546,285 B1 | 4/2003 | Owen et al. |
| 6,597,948 B1 | 7/2003 | Rockwell et al. |
| 6,602,191 B2 | 8/2003 | Quy |
| 6,681,003 B2 | 1/2004 | Linder et al. |
| 6,694,191 B2 | 2/2004 | Starkweather et al. |
| 6,804,554 B2 | 10/2004 | Ujhelyi et al. |
| 6,889,078 B2 | 5/2005 | Struble et al. |
| 6,889,079 B2 | 5/2005 | Bocek et al. |
| 6,908,437 B2 | 6/2005 | Bardy |
| 6,920,354 B2 | 7/2005 | Daynes et al. |
| 7,088,233 B2 | 8/2006 | Menard |
| 7,149,579 B1 | 12/2006 | Koh et al. |
| 7,231,258 B2 | 6/2007 | Moore et al. |
| 7,340,296 B2 | 3/2008 | Stahmann et al. |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,712,373 B2 | 5/2010 | Nagle et al. |
| 7,769,465 B2 | 8/2010 | Matos |
| 7,831,303 B2 | 11/2010 | Rueter et al. |
| 7,953,478 B2 | 5/2011 | Vaisnys et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,319,632 B1 | 11/2012 | Vaisnys et al. |
| 8,364,221 B2 | 1/2013 | Mannheimer et al. |
| 8,369,944 B2 | 2/2013 | Macho et al. |
| 8,406,842 B2 | 3/2013 | Kaib et al. |
| 8,548,584 B2 | 10/2013 | Jorgenson |
| 8,644,925 B2 | 2/2014 | Volpe et al. |
| 8,649,861 B2 | 2/2014 | Donnelly et al. |
| 8,676,313 B2 | 3/2014 | Volpe et al. |
| 8,706,215 B2 | 4/2014 | Kaib et al. |
| 8,768,441 B2 | 7/2014 | De Zwart et al. |
| 8,774,917 B2 | 7/2014 | Macho et al. |
| 8,880,196 B2 | 11/2014 | Kaib |
| 8,897,860 B2 | 11/2014 | Volpe et al. |
| 8,904,214 B2 | 12/2014 | Volpe et al. |
| 9,283,399 B2 | 3/2016 | Donnelly et al. |
| 9,381,373 B2 | 7/2016 | Geheb et al. |
| 10,674,911 B2 | 6/2020 | Freeman et al. |
| 2001/0031991 A1 | 10/2001 | Russial |
| 2001/0047140 A1 | 11/2001 | Freeman |
| 2002/0181680 A1 | 12/2002 | Linder et al. |
| 2003/0004547 A1 | 1/2003 | Owen et al. |
| 2003/0032988 A1 | 2/2003 | Fincke |
| 2003/0095648 A1 | 5/2003 | Kaib et al. |
| 2003/0109904 A1 | 6/2003 | Silver et al. |
| 2003/0158593 A1 | 8/2003 | Heilman et al. |
| 2003/0212311 A1 | 11/2003 | Nova et al. |
| 2004/0049233 A1 | 3/2004 | Edwards |
| 2004/0111122 A1 | 6/2004 | Daynes et al. |
| 2004/0127774 A1 | 7/2004 | Moore et al. |

(56) References Cited

U.S. PATENT DOCUMENTS

| | | |
|---|---|---|
| 2004/0133242 A1 | 7/2004 | Chapman et al. |
| 2005/0085258 A1 | 4/2005 | Ishii et al. |
| 2005/0131465 A1 | 6/2005 | Freeman et al. |
| 2005/0246199 A1 | 11/2005 | Futch |
| 2005/0283198 A1 | 12/2005 | Haubrich et al. |
| 2006/0095091 A1 | 5/2006 | Drew et al. |
| 2006/0173498 A1 | 8/2006 | Banville et al. |
| 2006/0211934 A1 | 9/2006 | Hassonjee et al. |
| 2006/0259080 A1 | 11/2006 | Vaisnys et al. |
| 2007/0129769 A1 | 6/2007 | Bourget et al. |
| 2007/0233199 A1 | 10/2007 | Moore et al. |
| 2007/0299473 A1 | 12/2007 | Matos |
| 2008/0004663 A1 | 1/2008 | Jorgenson |
| 2008/0033495 A1 | 2/2008 | Kumar |
| 2008/0058884 A1 | 3/2008 | Matos |
| 2008/0097793 A1 | 4/2008 | Dicks et al. |
| 2008/0114406 A1 | 5/2008 | Hampton et al. |
| 2008/0191893 A1 | 8/2008 | Li et al. |
| 2008/0233925 A1 | 9/2008 | Sun et al. |
| 2008/0249591 A1 | 10/2008 | Gaw et al. |
| 2008/0266118 A1 | 10/2008 | Pierson et al. |
| 2008/0287749 A1 | 11/2008 | Reuter |
| 2008/0306560 A1 | 12/2008 | Macho et al. |
| 2008/0306562 A1 | 12/2008 | Donnelly et al. |
| 2008/0312709 A1 | 12/2008 | Volpe et al. |
| 2009/0005827 A1 | 1/2009 | Weintraub et al. |
| 2009/0058636 A1 | 3/2009 | Gaskill et al. |
| 2009/0073991 A1 | 3/2009 | Landrum et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076559 A1 | 3/2009 | Libbus et al. |
| 2009/0146822 A1 | 6/2009 | Soliman |
| 2009/0232286 A1 | 9/2009 | Hurwitz |
| 2009/0234410 A1 | 9/2009 | Libbus et al. |
| 2009/0264792 A1 | 10/2009 | Mazar |
| 2009/0292194 A1 | 11/2009 | Libbus et al. |
| 2009/0312650 A1 | 12/2009 | Maile et al. |
| 2010/0052892 A1 | 3/2010 | Allen et al. |
| 2010/0052897 A1 | 3/2010 | Allen et al. |
| 2010/0069735 A1 | 3/2010 | Berkner |
| 2010/0076533 A1 | 3/2010 | Dar et al. |
| 2010/0268304 A1 | 10/2010 | Matos |
| 2010/0295674 A1 | 11/2010 | Hsieh et al. |
| 2010/0298899 A1 | 11/2010 | Donnelly et al. |
| 2010/0305462 A1 | 12/2010 | Callas et al. |
| 2010/0312297 A1 | 12/2010 | Volpe et al. |
| 2010/0324612 A1 | 12/2010 | Matos |
| 2011/0022105 A9 | 1/2011 | Owen et al. |
| 2011/0080294 A1 | 4/2011 | Tanishima et al. |
| 2011/0170692 A1 | 7/2011 | Konrad et al. |
| 2011/0172550 A1 | 7/2011 | Martin et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0060030 A1 | 3/2012 | Lamb |
| 2012/0112903 A1 | 5/2012 | Kaib et al. |
| 2012/0116272 A1 | 5/2012 | Hampton et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2012/0302860 A1 | 11/2012 | Volpe et al. |
| 2013/0013014 A1 | 1/2013 | Donnelly et al. |
| 2013/0060149 A1 | 3/2013 | Song et al. |
| 2013/0085538 A1 | 4/2013 | Volpe et al. |
| 2013/0144355 A1 | 6/2013 | Macho et al. |
| 2013/0218252 A1 | 8/2013 | Kaib et al. |
| 2013/0231711 A1 | 9/2013 | Kaib |
| 2013/0324868 A1 | 12/2013 | Kaib et al. |
| 2013/0325078 A1 | 12/2013 | Whiting et al. |
| 2013/0325096 A1 | 12/2013 | Dupelle et al. |
| 2014/0004814 A1 | 1/2014 | Elghazzawi |
| 2014/0005736 A1 | 1/2014 | Geheb |
| 2014/0031885 A1 | 1/2014 | Elghazzawi et al. |
| 2014/0121717 A1 | 5/2014 | Geheb et al. |
| 2014/0163334 A1 | 6/2014 | Volpe et al. |
| 2014/0206974 A1 | 7/2014 | Volpe et al. |
| 2014/0277243 A1 | 9/2014 | Maskara et al. |
| 2014/0303680 A1 | 10/2014 | Donnelly et al. |
| 2014/0324112 A1 | 10/2014 | Macho et al. |
| 2015/0035654 A1 | 2/2015 | Kaib et al. |
| 2015/0039039 A1 | 2/2015 | Macho et al. |
| 2015/0039042 A1 | 2/2015 | Amsler et al. |
| 2015/0039053 A1 | 2/2015 | Kaib et al. |
| 2015/0067769 A1 | 3/2015 | Barton et al. |
| 2015/0080699 A1 | 3/2015 | Kaib et al. |
| 2015/0149776 A1 | 5/2015 | Chastain et al. |
| 2015/0224330 A1 | 8/2015 | Kaib et al. |
| 2016/0110567 A1 | 4/2016 | Rooyakkers et al. |
| 2016/0226865 A1 | 8/2016 | Chen et al. |
| 2017/0075699 A1 | 3/2017 | Narayanan et al. |

FOREIGN PATENT DOCUMENTS

| | | |
|---|---|---|
| EP | 1642616 | 4/2006 |
| JP | 11-149379 | 6/1999 |
| JP | 2002509472 | 3/2002 |
| JP | 2002-514107 | 5/2002 |
| JP | 2004-318839 | 11/2004 |
| JP | 2008-302228 | 12/2008 |
| JP | 2008302225 | 12/2008 |
| JP | 2009510631 | 3/2009 |
| JP | 2009-521865 | 6/2009 |
| JP | 2009-528909 | 8/2009 |
| JP | 2012-003311 | 1/2012 |
| WO | 8304171 | 12/1983 |
| WO | 1997022297 | 6/1997 |
| WO | 1998039061 | 9/1998 |
| WO | 2000030529 | 6/2000 |
| WO | 2004078259 | 9/2004 |
| WO | 2007019325 | 2/2007 |
| WO | 2009034506 | 3/2009 |
| WO | 2009122277 | 10/2009 |
| WO | 2012006524 | 1/2012 |
| WO | 2012100219 | 7/2012 |
| WO | 2013130957 | 9/2013 |
| WO | 2014018160 | 1/2014 |
| WO | 2014097035 | 6/2014 |

OTHER PUBLICATIONS

American Journal of Respiratory and Critical Care Medicine, "ATS Statement: Guidelines for the Six-Minute Walk Test" vol. 166, pp. 111-117, 2002, American Thoracic Society, available at URL:http://ajrccm.atsjournals.org/cgi/content/ull/166/1/111.

C. Shane Reid, "Customer- or Patient-Based Selective Data Encryption in Medical Device Management", U.S. Appl. No. 15/084,367, filed Mar. 16, 2016, 83 pages.

European Search Report for EP Application 13808725.9 mailed on Jan. 25, 2016, 7 pages.

Freeman et al, "Establishing Secure Communication at an Emergency Care Scene", U.S. Appl. No. 15/464,515, filed Mar. 21, 2017, 89 pages.

http:/web.archive.org/web/20030427001846/http:/lifecor.comiimagelib/imageproduct.asp.; Published by LifeCor, Inc., 2002, on a web page owned by LifeCor, Inc.

Ian Durrant, "Clinical Data Handoff In Device Management and Data Sharing", U.S. Appl. No. 15/084,249, filed Mar. 29, 2016, 78 pages.

International Search Report and Written Opinion for PCT Application No. PCT/US2013/047617 mailed on Nov. 12, 2013.

International Search Report and Written Opinion from corresponding PCT Application No. PCT/US2012/030428, mailed on Nov. 7, 2012.

(56) References Cited

OTHER PUBLICATIONS

International Search Report and Written Opionion from PCT Application No. PCT/US2013/028598 mailed on May 9, 2013.
Timothy F. Stever, "Patient Data Hub", U.S. Appl. No. 62/315,439, filed Mar. 30, 2016, 39 pages.
Zoll Medical Corporation, "LifeVest Model WCD 3000 Operator's Manual", Pittsburgh, PA.

SYSTEMS AND METHODS OF INTEGRATING AMBULATORY MEDICAL DEVICES

RELATED APPLICATIONS

This application claims the benefit under 35 U.S.C. § 120 as a continuation of U.S. patent application Ser. No. 16/862,752, titled "SYSTEMS AND METHODS OF INTEGRATING AMBULATORY MEDICAL DEVICES," filed on Apr. 30, 2020, which claims the benefit under 35 U.S.C. § 120 as a continuation of U.S. patent application Ser. No. 15/472,485, titled "SYSTEMS AND METHODS OF INTEGRATING AMBULATORY MEDICAL DEVICES," filed Mar. 29, 2017 which claims priority under 35 U.S.C. § 119(e) to U.S. Provisional Application No. 62/315,486, titled "SYSTEMS AND METHODS OF INTEGRATING AMBULATORY MEDICAL DEVICES", filed Mar. 30, 2016. Each of these related applications is hereby incorporated herein by reference in its entirety.

BACKGROUND

This disclosure relates generally to external medical devices, and more specifically, to apparatus and processes that integrate ambulatory medical devices with hospital medical devices.

There are a wide variety of electronic and mechanical medical devices for monitoring and treating patients' medical conditions. The one or more particular medical devices used to monitor and/or treat a patient depend on the underlying medical condition with which the patient is afflicted. For example, where a patient has a medical condition that affects the patient's cardiac function (e.g., a cardiac arrhythmia), medical devices such as cardiac pacemakers or defibrillators may be used to treat the patient. In some cases, these medical devices may be surgically implanted or externally connected to the patient. Such medical devices may be used alone, or in combination with drug therapies, to treat medical conditions such as cardiac arrhythmias.

One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can be administered. Other cardiac arrhythmias include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

Some medical devices operate by continuously or substantially continuously monitoring the patient's heart for treatable arrhythmias via one or more sensing electrodes and, when such is detected, applying corrective electrical pulses directly to the heart through one or more therapy electrodes. Patients use these devices while ambulatory and visiting various locations, such as their home or place of work.

SUMMARY

An ambulatory medical device stores a wealth of data regarding a patient that is potentially useful to a hospital practitioner when caring for the patient. Examples of this patient data include data descriptive of patient activity, compliance, body position, electrocardiogram (ECG) readings, heart sounds, respiration, blood oxygen level, and other patient parameters. Patient data may also include patient demographic data (e.g., name, address, insurance provider, etc.), data descriptive of healthcare provider observations of the patient, and images of the patient. Both the hospital practitioner and patient may further benefit from granting control of the ambulatory medical device upon the patient's entry into the hospital. This is especially true where the ambulatory medical device is configured to provide treatment to the patient that may be manually initiated by the hospital practitioner in an emergency. Further, publication of the data, along with data generated by other medical devices located in the hospital, can be used to construct a patient dashboard summarizing the patient's condition over time and illustrating a chronology of care provided to the patient via the ambulatory medical device and the other medical devices located in the hospital. This chronology may both inform a caregiver's treatment of the patient in an emergency and be studied to prescribe an extended course of treatment to the patient.

In one example, an ambulatory medical device is provided. The ambulatory medical device includes at least one sensor configured to acquire physiological data of a patient, at least one network interface and at least one processor coupled to the at least one sensor and the at least one network interface. The at least one processor is configured to detect, via the at least one network interface, a medical device, to establish a secure communication session with the medical device via the at least one network interface, to detect a data capacity of the secure communication session, to identify a category of patient data associated with the data capacity, and to transmit patient data of the category to the medical device via the secure communication session.

In the ambulatory medical device, the at least one processor may be configured to detect the medical device in response to the ambulatory medical device entering a predefined range of the medical device. The at least one processor may be configured to determine whether the medical device is trusted prior to establishing the secure communication session.

In the ambulatory medical device, the patient data may include a summary based on electrocardiogram data. The summary may describe a heart rate of the patient. The at least one processor may be configured to monitor the data capacity and to include electrocardiogram data within the patient data where the data capacity exceeds a predetermined threshold.

The ambulatory medical device may further include at least one electrode configured to shock the patient. The ambulatory medical device may further include a garment housing the at least one electrode. In the ambulatory medical device, the at least one processor may be configured to determine whether the medical device is within the predefined range based on at least one of a Wi-Fi signal strength, a BLUETOOTH signal strength, and a near field communication signal strength. The at least one processor may be configured to determine that the medical device is within the predefined range based on physical contact between the medical device and at least one of the ambulatory medical device and the patient.

In the ambulatory medical device, the at least one processor may be configured to receive instructions to treat the patient from the medical device and to execute the instructions to treat the patient. The at least one processor may be configured to implement a web server to receive the instructions within the secure communication session. The at least one processor may be configured to receive instructions to execute a diagnostic protocol from the medical device and to execute the diagnostic protocol. The ambulatory medical may further include a user interface coupled to the at least one processor, the diagnostic protocol may include a six-minute walk test and the at least one processor may be configured to prompt the user, via the user interface, to perform the six-minute walk test.

In the ambulatory medical device, the at least one processor may be configured to implement a web server to transmit the patient data to a programmable device distinct from the medical device and the ambulatory medical device. The programmable device may include at least one of a mobile computing device, a remote server, and a hospital data system. The patient data may include compliance data. The at least one processor may be configured to detect a predefined patient condition and to transmit instructions for the medical device to issue an alert via a user interface regarding the patient condition.

In another example, a hospital medical device is provided. The hospital medical device includes at least one network interface and at least one processor coupled to the at least one network interface. The at least one processor is configured to detect, via the at least one network interface, an external ambulatory medical device; to establish a secure communication session with the external ambulatory medical device via the at least one network interface; to receive patient summary data via the secure communication session; and to process the patient summary data.

In the hospital medical device, the at least one processor may be configured to request, in response to processing the patient summary data, detailed data upon which the summary data is based from the external ambulatory medical device via the secure communication session. The at least one processor may be configured to transmit patient data to the external ambulatory medical device via the secure communication session. The hospital medical device may include at least one of a defibrillator, a temperature management system, a ventilator, a resuscitation system, and a telemetry system.

In the hospital medical device, the patient summary data may be based on electrocardiogram data. The patient summary data may describe a heart rate of the patient. The at least one processor may be configured to determine whether the external ambulatory medical device is within a predefined range of the hospital medical device based on at least one of a Wi-Fi signal strength, a BLUETOOTH signal strength, and a near field communication signal strength. The at least one processor may be configured to determine the external ambulatory medical device is within a predefined range based on physical contact between the hospital medical device and at least one of the external ambulatory medical device and the patient.

The hospital medical device may further include a user interface coupled to the at least one processor. The at least one processor may be configured to receive input via the user interface, to generate instructions to treat the patient based on the input, and to transmit the instructions to the external ambulatory medical device. The at least one processor may be configured to implement a web server to transmit the instructions within the secure communication session. The at least one processor may be configured to receive input via the user interface, to generate instructions to execute a diagnostic protocol based on the input, and to transmit the instructions to the external ambulatory medical device. The diagnostic protocol may include a six-minute walk test. The at least one processor may be configured to receive instructions from the external ambulatory medical device to issue an alert via the user interface regarding a patient condition. The at least one processor may be configured to display patient data on the user interface.

In the hospital medical device, wherein the at least one processor may be configured to implement a web server to transmit patient data to a programmable device distinct from the hospital medical device and the external ambulatory medical device. The programmable device may include at least one of a mobile computing device, a remote server, and a hospital information system. The patient data may include compliance data.

In another example, a system of medical devices is provided. The system includes an external ambulatory medical device and a hospital medical device. The external ambulatory medical device includes one or more network interfaces and at least one sensor configured to acquire physiological data of a patient. The hospital medical device includes at least one network interface and at least one processor coupled to the at least one network interface. The at least one processor is configured to detect, via the at least one network interface, the external ambulatory medical device; to establish a secure communication session with the external ambulatory medical device via the at least one network interface; to receive patient summary data via the secure communication session; to process the patient summary data.

In the system of medical devices, the at least one processor of the hospital medical device may be configured to request, in response to processing the patient summary data, detailed data upon which the patient summary data is based from the external ambulatory medical device via the secure communication session. The external ambulatory medical device may include one or more processors configured to limit transmission of patient data at least in part by calculating the patient summary data, transmitting the patient summary data to the hospital medical device, receiving a request for detailed data, and transmitting, in response to receiving the request, the detailed data to the hospital medical device.

In the system, the hospital medical device may include a resuscitation system, the external ambulatory medical device may include an accelerometer, and the at least one processor of the hospital medical device may be configured to receive location tracking data measured by the accelerometer and to detect whether chest compressions are of a correct depth using the location tracking data.

In the system, the hospital medical device may include a temperature management system, the external ambulatory medical device may include a temperature sensor configured to measure a body temperature of the patient, and the at least one processor may be configured to receive body temperature data measured by the temperature sensor and to detect whether the body temperature transgresses a threshold.

In the system, the at least one processor may be configured to receive electrocardiogram data and to process the electrocardiogram data to generate the patient summary data. The hospital medical device may further include a user interface coupled to the at least one processor. The at least one processor may be configured to display, on a screen of the user interface, data originated by the hospital medical device and display, on the screen of the user interface, data originated by the external ambulatory medical device.

In another example, a method of integrating an ambulatory medical device with a hospital medical device is provided. The method includes acts of acquiring, by the ambulatory medical device, physiological data of a patient; detecting, by the ambulatory medical device, the hospital medical device; establishing a secure communication session between the ambulatory medical device and the hospital medical device; detecting, by the ambulatory medical device, a data capacity of the secure communication session; identifying, by the ambulatory medical device, a category of patient data associated with the data capacity; and transmitting, by the ambulatory medical device, patient data of the category to the hospital medical device via the secure communication session.

In the method, the act of detecting the hospital medical device may include an act of detecting the hospital medical device in response to the ambulatory medical device entering a predefined range of the hospital medical device. The method may further include an act of determining whether the hospital medical device is trusted prior to establishing the secure communication session. In the method, the act of transmitting the patient data may include an act of transmitting a summary based on electrocardiogram data.

Still other aspects, examples and advantages of these aspects and examples, are discussed in detail below. Moreover, it is to be understood that both the foregoing information and the following detailed description are merely illustrative examples of various aspects and features, and are intended to provide an overview or framework for understanding the nature and character of the claimed aspects and examples. Any example or feature disclosed herein may be combined with any other example or feature. References to different examples are not necessarily mutually exclusive and are intended to indicate that a particular feature, structure, or characteristic described in connection with the example may be included in at least one example. The appearances of such terms herein are not necessarily all referring to the same example.

DESCRIPTION OF DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of any particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1:
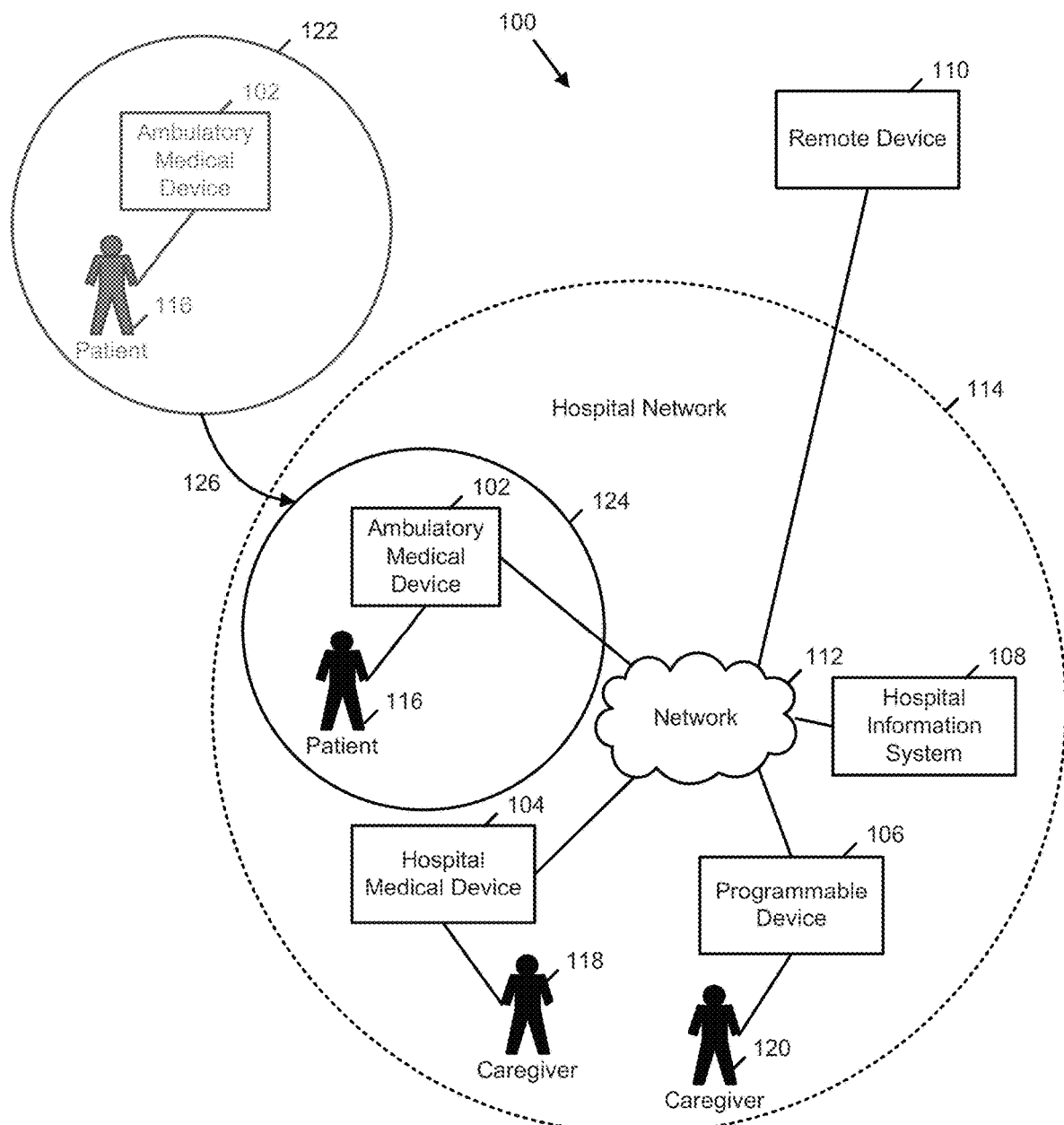
FIG. 1 is a schematic diagram of one example of a distributed computer system in accordance with an example of the present disclosure.

Some aspects and examples are directed to apparatus and processes that monitor a hospital environment for the introduction of trusted ambulatory medical devices and integrate the trusted medical devices with hospital medical devices to enhance patient care. In some examples, hospital medical devices and/or ambulatory medical devices monitor for and detect one another when they are brought into close physical proximity. Further, in these examples, the medical devices establish a trusted relationship and execute one or more secure communication sessions in which the medical devices exchange data and/or instructions. As a result of this interoperation, patient data is efficiently shared between the medical devices, thereby enabling the medical device to better treat the patient individually or in combination. In addition, in some examples, the medical devices publish patient data to a distinct programmable device. In these examples, the distinct programmable device processes the patient data to provide a chronology of care that spans multiple medical devices. Such a rapidly assembled set of information may be valuable in some clinical situations, such as where a healthcare professional or other caregiver in an emergency room is presented with a patient whose care is time critical in nature.

Examples of the methods and systems discussed herein are not limited in application to the details of construction and the arrangement of components set forth in the following description or illustrated in the accompanying drawings. The methods and systems are capable of implementation in other examples and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, components, elements or acts of the systems and methods herein referred to in the singular may also embrace examples including a plurality, and any references in plural to any example, component, element or act herein may also embrace examples including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated references is supplementary to that of this document; for irreconcilable inconsistencies, the term usage in this document controls.

Hospital Environment

FIG. 1 is a schematic diagram that illustrates the components and operation of a distributed computing system 100 within a hospital when configured in accordance with at least one example. As shown, the distributed computing system 100 includes an ambulatory medical device 102, a hospital medical device 104, a programmable device 106, a hospital information system 108, a remote device 110, and a communication network 112. The ambulatory medical device 102 is configured to monitor and/or treat the patient 116. In some examples in accordance with FIG. 1, the hospital medical device 104 is associated with and operated by the caregiver 118 and the programmable device 106 is associated with and operated by the caregiver 120. The characteristics of these devices and their methods of interoperation and integration are described further below.

In some examples, the ambulatory medical device 102 is worn by the patient 116 and includes sensors that monitor the physiology of the patient 116 over, in some instances, an extended time period (e.g., a few hours, days, weeks, or even months). The ambulatory medical device 102 may also include treatment components, such as treatment electrodes, that are configured to treat the patient when warranted. Particular examples of the ambulatory medical device 102 include, among other devices, mobile cardiac telemetry devices, sleep apnea devices, drug delivery devices, oxygen concentrators, mobile cardiac telemetry devices and/or wearable defibrillators, such as the LifeVest® brand wearable defibrillator available from ZOLL® Medical Corporation.

The hospital medical device 104 may include any of a variety of hospital equipment used by caregivers (doctors, nurses, medical technicians, etc.) to monitor and/or treat patients in a hospital setting. The hospital medical device 104 includes sensors that detect physiological signals and may, like the ambulatory medical device 102, include treatment components. Particular examples of the hospital medical device 104 include patient monitoring devices and patient treatment devices, for example monitor defibrillators (e.g., R Series® brand monitor defibrillators available from ZOLL® Medical Corporation), resuscitation systems (e.g., AutoPulse® resuscitation systems available from ZOLL® Medical Corporation), temperature management systems (e.g., Thermogard XP® temperature management systems available from ZOLL® Medical Corporation), ventilators (e.g., Eagle II™ portable ventilator), and hospital telemetry systems.

In some examples, the remote device 110 and the programmable device 106 are programmable devices used by caregivers to access data regarding the patients, such as the patient 116. These devices include a processor and memory coupled to the processor. Specific examples of the remote device 110 include a remote server that is a part of the LifeVest® network service provided by ZOLL® Medical Corporation. As such, in some examples, the remote device 110 is configured to receive, store, and provide patient data to other devices (e.g., the programmable device 106) via, for example, a web server. Specific examples of the programmable device 106 include smartphones, tablet computers, laptop computers, and other computing devices. The hospital information system (HIS) 108 may include one or more programmable devices that are configured to provide a hospital with data processing that supports administrative, financial, medical, and legal operations of the hospital.

As shown in FIG. 1, the network 112 supports a communication range 114 within which programmable devices may connect to and communicate with one another. The size of the communication range 114 varies between examples and depends on the underlying network technology used to implement the network 112. Example network technology used to implement the network 112 may include one or more of cellular, Wi-Fi, BLUETOOTH, near field communication, body area network technology, and wired local area network technology. In some examples, the communication range is coterminous with the physical structure of the hospital or hospital department (e.g., Emergency Department).

In FIG. 1, the ambulatory medical device 102 and the patient 116 are illustrated in two distinct positions. One position 122 resides outside the communication range 114. Another position 124 resides inside the communication range 114. Arrow 126 illustrates the movement of the medical device 102 and the patient 116 from the position 122 to the position 124. As is described further below, in some examples, the transition of the ambulatory medical device 102 from the area outside the communication range 114 to the area inside the communication range 114 is detected by the hospital medical device 104 and/or the ambulatory medical device 102 via, for example, a signal strength of the network 112.

Various examples disclosed herein are configured to respond to detection of this transition by executing one or more of a variety of integration processes. These integration processes provide a variety of benefits. By aggregating patient data into a single device and/or user interface, the integration processes provide caregivers with a comprehensive source of information regarding patient history and treatment. Where the single device and/or user interface is familiar to the caregiver (e.g., where the integration processes collocate patient data in a hospital device that the caregiver is trained to operate), the caregiver is able to quickly identify information important to the treatment of the patient. In addition, the integration processes provide for rapid distribution of patient data to, in some cases, experts at remote locations who can use the patient data to help hospital caregivers diagnose and treat the patient.

Figure 2:
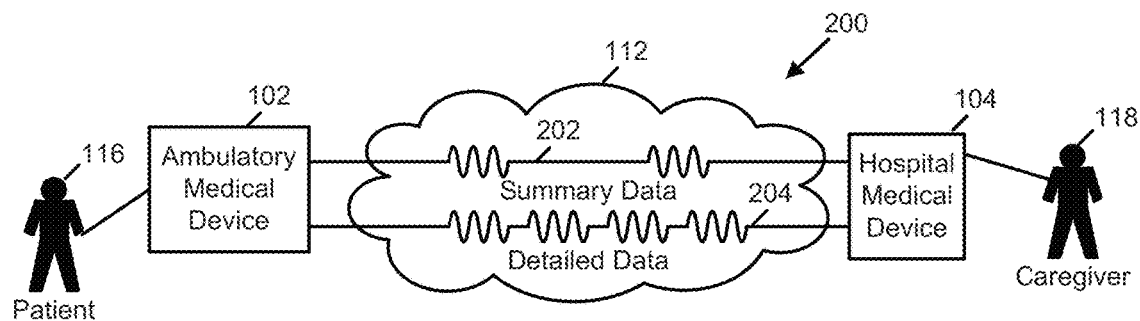
FIG. 2 is schematic diagram of a patient data communication session in accordance with an example of the present disclosure.

One of the integration processes disclosed herein implements a secure transfer of patient data from the ambulatory medical device 102 to the hospital medical device 104. FIG. 2 illustrates the components involved in this secure transfer. As shown, the ambulatory medical device 102 is configured to transmit summary patient data 202 and/or detailed patient data 204 to the hospital medical device 104 within a secure communication session 200. The detailed data may include high resolution data, such as ECG data. The summary data may be generated by a predetermined summary process executed on the detailed data and may include calculated summaries of the detailed data, such as heartbeat and/or heart rate data, arrhythmia determinations and detection alerts, etc. The secure communication session 200 may be implemented via the network 112 using, for example, an encrypted tunnel between the medical devices 102 and 104. In addition, in some examples, any of the communication sessions described herein (e.g., secure communication sessions 200, 300, and 400) may be implemented using the techniques described in commonly owned U.S. Patent Application Ser. No. 62/315,553, titled ESTABLISHING SECURE COMMUNICATION AT AN EMERGENCY CARE SCENE, filed on Mar. 30, 2016, which is hereby incorporated herein by reference in its entirety. In some examples, the hospital medical device 104 presents the received patient data via a user interface individually or in conjunction with additional data generated by the hospital medical device 104. Further, in some examples, the ambulatory medical device 102 is configured to selectively transmit the summary data 202 and/or the detailed data 204 based on a measured data capacity of the secure communication session 200. Further description of patient data communication processes that the medical devices 102 and 104 are configured to execute is provided below with reference to FIGS. 8-11.

In some examples illustrated by FIG. 2, the hospital medical device 104 monitors patient data received, in real time, and issues alerts generated by the ambulatory medical device 102 and/or instructs the caregiver 118 regarding treatment of the patient 116. For instance, in one example where the hospital medical device 104 is a resuscitation system, the hospital medical device 104 may use accelerometer data received from the ambulatory medical device 102 to detect whether chest compressions are of the correct depth and/or rate to be effective. In this example, the hospital medical device 104 may request, via a user interface, that the caregiver 118 make adjustments. In another example where the hospital medical device 104 is a temperature management system, the hospital medical device 104 may use vital signs data (e.g., data descriptive of patient body temperature) received from the ambulatory medical device 102 to manage the patient's temperature. In some examples, the hospital medical device 104 may monitor the patient 116 during performance of a diagnostic protocol (e.g., a six-minute walk test) and display patient data acquired by the ambulatory medical device 102 on a user interface of the hospital medical device 104.

Figure 3:
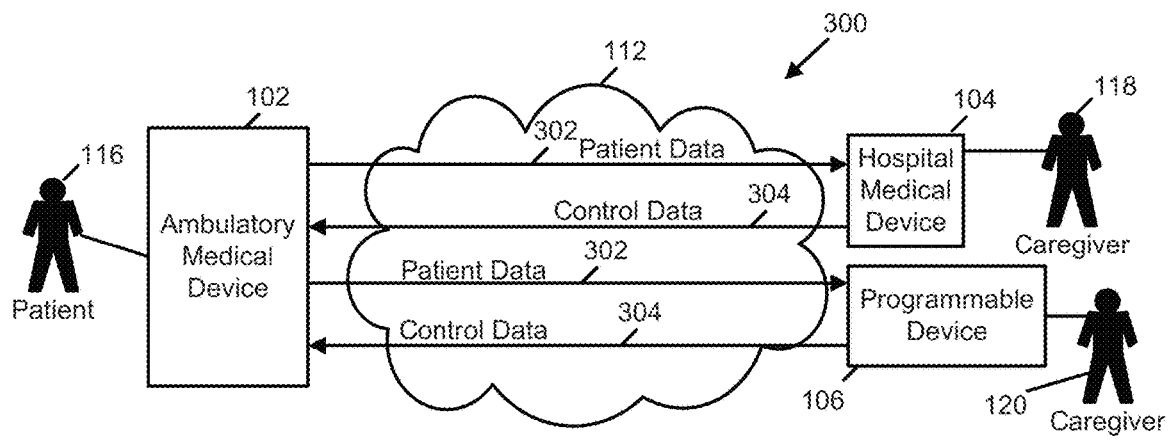
FIG. 3 is a schematic diagram of a control communication session in accordance with an example of the present disclosure.

Another integration process implements a secure control session in which the hospital medical device 104 and/or the programmable device 106 controls operation of the ambulatory medical device 102. FIG. 3 illustrates the components involved in this secure control session. As shown, the ambulatory medical device 102 is configured to transmit patient data 302 to the hospital medical device 104 and/or the programmable device 106 within a secure control session 300. The patient data 302 may include summary data 202 and/or detailed data 204 as described above with reference to FIG. 2. The secure control session 300 may be implemented via the network 112 using, for example, an encrypted tunnel between the medical devices 102 and 104 and/or between the medical device 102 and the programmable device 106. In some examples, the hospital medical device 104 and/or the programmable device 106 is configured to receive the patient data, process the patient data, and transmit control data 304 generated by the processing of the patient data to the ambulatory medical device 102. In these examples, the ambulatory medical device 102 is further configured to receive the control data 304, process the control data 304, and execute one or more operations requested in the control data 304. Further description of secure control processes that the medical devices 102 and 104 and the programmable device 106 are configured to execute is provided below with reference to FIGS. 8-11.

Figure 4:
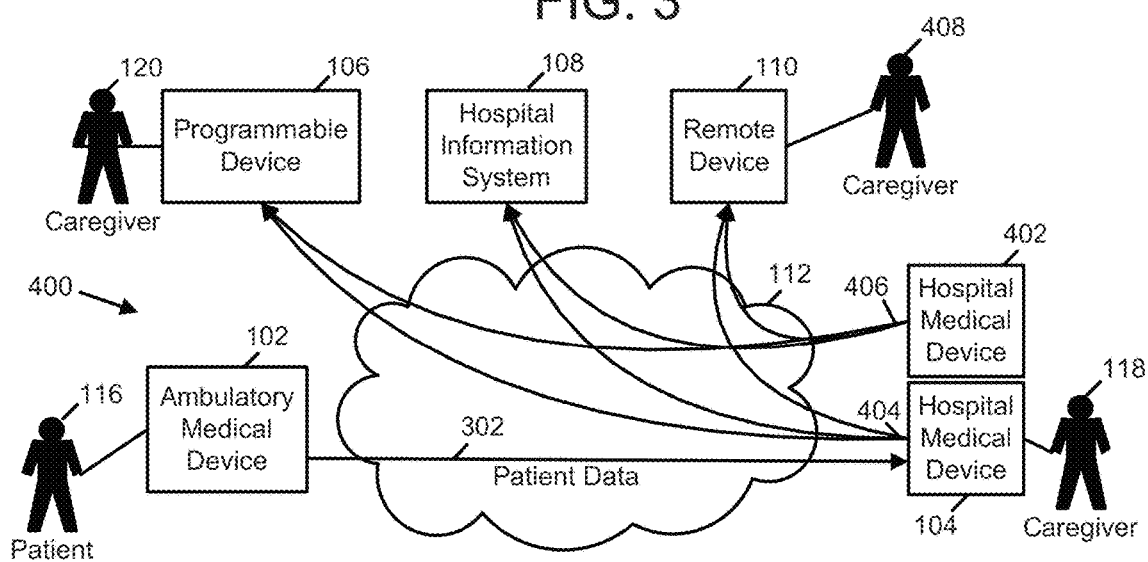
FIG. 4 is a schematic diagram of a patient data publication session in accordance with an example of the present disclosure.

Another integration process implements a secure patient data publication session in which the hospital medical device 104 publishes patient data to the HIS 108, the programmable device 106, and/or the remote device 110. FIG. 4 illustrates the components involved in this secure publication session. As shown, the ambulatory medical device 102 is configured to transmit the patient data 302 to the hospital medical device 104 as described above with reference to FIG. 3. Further, as illustrated in FIG. 4, the hospital medical device 104 is configured to transmit the patient data 302 and/or processed patient data 404 to the HIS 108, the programmable device 106, and/or the remote device 110 via a secure publication session 400. The secure publication session 400 may be implemented via the network 112 using, for example, an encrypted tunnel between the hospital medical device 104 and each of the HIS 108, the programmable device 106, and/or the remote device 110. The secure publication session 400 may also be implemented via a network connection that is separate and distinct from any hospital network (e.g., via a cellular connection or other wireless connection). In some examples, another hospital medical device 402 is configured to transmit additional patient data 406 to the HIS 108, the programmable device 106, and/or the remote device 110 within the secure publication session 400. The additional patient data 406 may include patient data generated by the hospital medical device 402.

To meet security requirements of the HIS 108 in some examples, the secure publication session 400 may be conducted via a data hub compliant with one or more security standards, such as the Federal Information Processing Standard (FIPS). In these examples, the hospital medical device 104 and/or the hospital medical device 402 may be configured to communicate sensitive patient data (e.g., compliance data, ECG data, demographic data and images of the patient) to the HIS 108 via a patient data hub as described in U.S. Patent Application Ser. No. 62/315,439, titled PATIENT DATA HUB, filed Mar. 30, 2016, which is hereby incorporated herein by reference in its entirety.

In some examples, the remote device 110 is configured to receive the patient data 302, the processed patient data 404, and/or the additional patient data 406 and provide a user interface including information based on the patient data 302, the processed patient data 404, and/or the additional patient data 406. The user interface may be presented to a caregiver 408 who is available to remotely analyze the patient data and support the caregiver 118 treating of the patient 116. Alternatively or additionally, the user interface may be presented to the caregiver 120 via the programmable device 106. The user interface may present monthly trends and other historical patient data. One example a user interface provided by the remote device 110 is described further below with reference to FIG. 13. Further description of secure publication processes that the medical devices 102 and 104 are configured to execute is provided below with reference to FIGS. 8-11.

Example Ambulatory Medical Device

Figure 5:
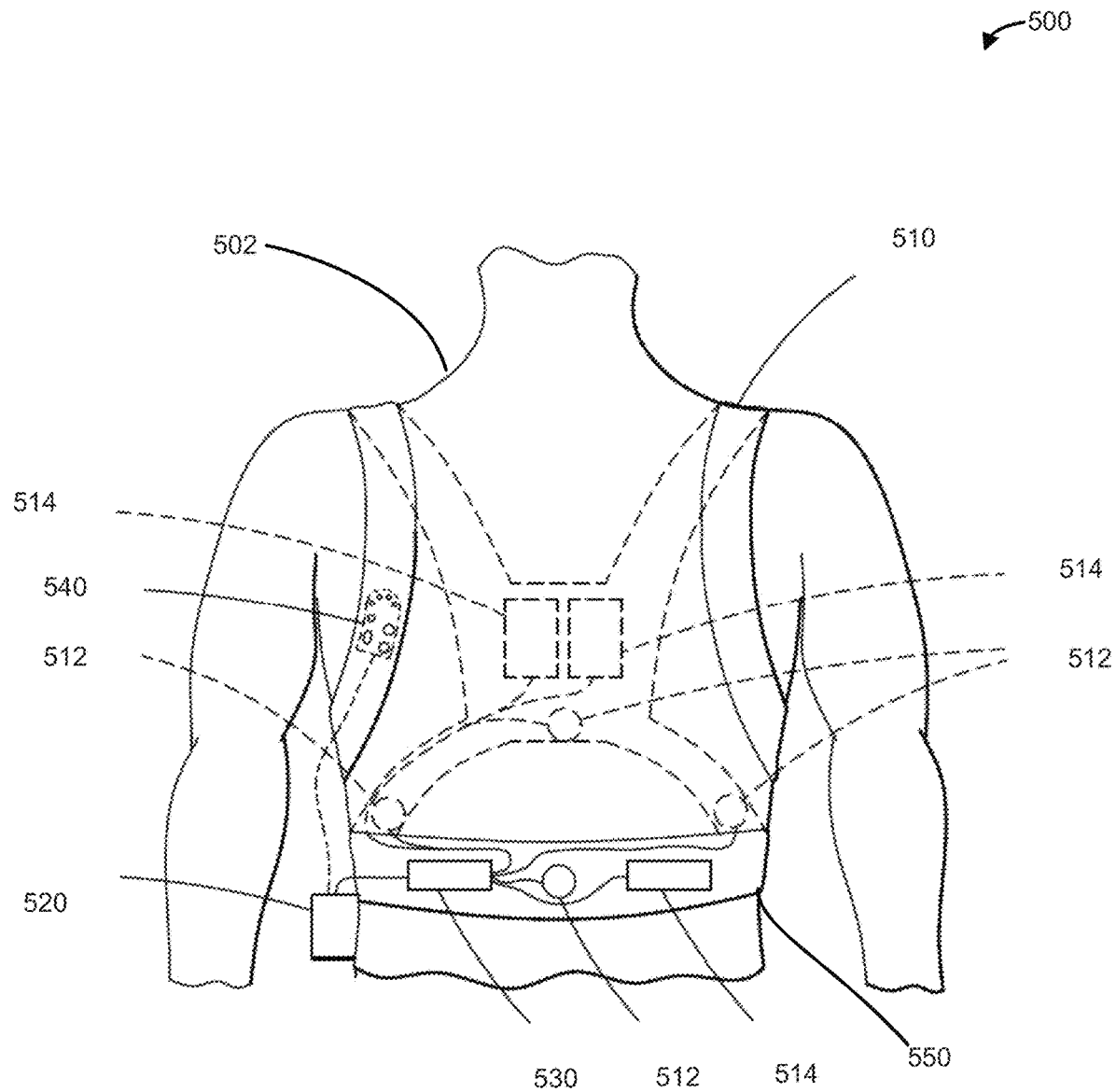
FIG. 5 is a schematic diagram of an ambulatory medical device in accordance with an example of the present disclosure.

In some implementations, the ambulatory medical device 102 is an external wearable defibrillator, such as the LifeVest® wearable defibrillator available from ZOLL® Medical Corporation. FIG. 5 illustrates an example medical device 500 that is external, ambulatory, and wearable by the patient 502. As shown, the medical device 500 includes a garment 510, a plurality of sensing electrodes 512, a plurality of therapy electrodes 514, a medical device controller 520, a connection pod 530, a patient interface pod 540, and a belt 550. The plurality of sensing electrodes 512 can be disposed at various positions about the patient's body. As shown, the sensing electrodes 512 are electrically coupled to the medical device controller 520 through the connection pod 530. In some implementations, some of the components of the wearable medical device 500 are affixed to the garment 510 that can be worn on the patient's torso. For example, as shown in FIG. 5, the controller 520, at least some of the sensing electrodes 512, and, optionally, one or more therapy electrodes 514 can be mounted on a belt 550 worn by the patient. The sensing electrodes 512 and the connection pod 530 can be assembled or integrated into the garment 510 as shown. The sensing electrodes 512 are configured to monitor the cardiac function of the patient (e.g., by monitoring one or more cardiac signals of the patient). The plurality of therapy electrodes 514 can be electrically coupled to the controller 520 through the connection pod 530. The therapy electrodes 514 are configured to deliver one or more therapeutic defibrillating shocks to the body of the patient if the medical device 500 and/or the hospital medical device 104 determines that such treatment is warranted. The connection pod 530 may include electronic circuitry and one or more sensors (e.g., a motion sensor, an accelerometer, etc.) that are configured to monitor patient activity.

The wearable medical device 500 may include the optional patient interface pod 540 that is coupled to the medical device controller 520. For example, the patient interface pod 540 may include patient interface elements such as a speaker, a microphone responsive to patient input, a display, an interactive touch screen responsive to patient input, and/or physical buttons for input. In some implementations, these elements are incorporated into a housing of the controller 520. In one example, the controller 520 is configured to detect whether the patient interface pod 540 is operatively coupled to the controller 520. In this example, the controller is further configured to disable the patient interface elements of the controller 520 and instead communicate with the patient via the patient interface pod 540. In certain examples, the patient interface pod 540 and the patient interface elements of controller 520 may serve as a redundant input mechanism through which the patient may interact with the controller 520. The patient interface pod 540 may be wirelessly coupled with the controller 520. The patient interface pod 540 may take other forms and include additional functionality. For instance, the patient interface pod 540 may be implemented on a smartphone, tablet, or other mobile device carried by the patient. In another example, the patient interface pod 540 may be worn as a watch about the wrist of the patient, or as a band about an upper arm of the patient. In some implementations, the controller 520 may communicate certain alerts and data and/or be responsive to patient input via both the patient interface elements included in the controller 520 and the patient interface pod 540. The patient and/or caregiver can interact with a touch display or the patient interface pod 540 to control the medical device 500.

Example Hospital Medical Device

Figure 6:
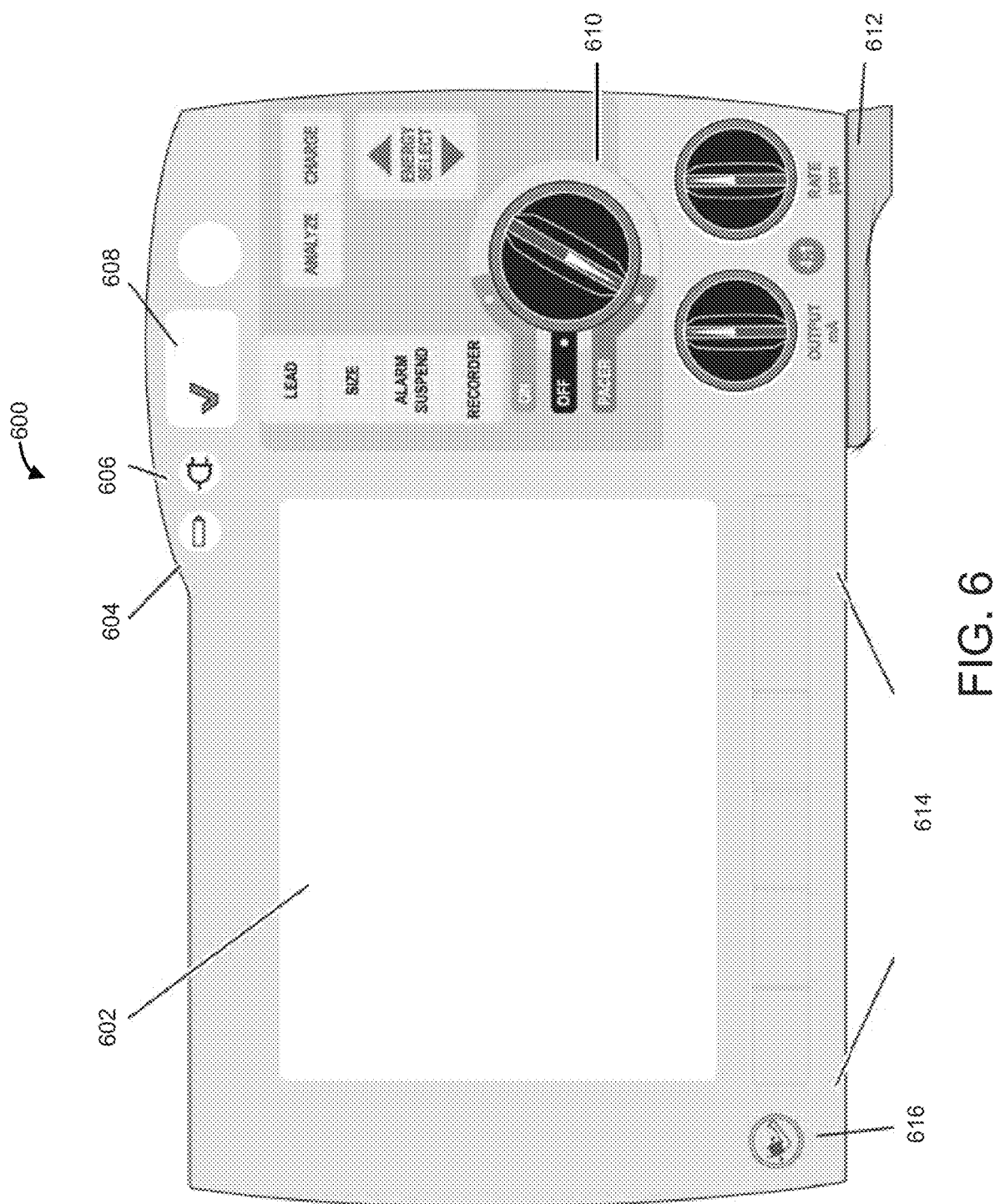
FIG. 6 is a schematic diagram of a hospital medical device in accordance with an example of the present disclosure.

In some examples, the hospital medical device 104 includes a monitor defibrillator or a patient monitoring device. Monitor defibrillators that are capable of monitoring cardiac rhythms, determining when a defibrillating shock is necessary, and administering the defibrillating shock either automatically, or under the control of a trained caregiver (e.g., the caregiver 118). The monitor defibrillator, in addition, may be configured to provide counseling to a caregiver as to how to perform cardiac resuscitation (CPR). FIG. 6 illustrates a monitor defibrillator 600. The monitor defibrillator 600 may be, for example, an R Series® brand monitor defibrillator available from ZOLL® Medical Corporation. As shown, the monitor defibrillator 600 a display screen 602, a battery indicator 604, an AC power indicator 606, a code readiness indicator 608, a mode selector 610, a pacer door 612, soft keys 614, and a NIBP button 616. Although not shown in FIG. 6, the monitor defibrillator 600 also includes an electrode assembly including one or more sensing electrodes (similar to the sensing electrodes 512), one or more therapy electrodes (similar to the therapy electrodes 514), and the electrically coupling required to operatively connect the electrodes to the monitor defibrillator 600.

The monitor defibrillator 600 is configured to detect the cardiac rhythm of a patient using ECG data and provide pacing and defibrillating shocks to the patient as appropriate. As shown in FIG. 6, the user interface of the monitor defibrillator 600 may include a variety of components configured to communicate with the caregiver. In some examples, the monitor defibrillator 600 is configured to display notifications to the caregiver via the display screen 602. These notifications may be based on patient data provided by the ambulatory medical device 102 and may provide instructions to the caregiver regarding the proper administration of CPR to the subject. The notifications may also include patient data provided by the ambulatory medical device 102. The notifications on the display screen 602 may be accompanied by audible alerts from a speaker to further assist the caregiver in administering CPR to the patient.

The examples of hospital medical devices are not limited to the monitor defibrillator 600 described above. Other example hospital medical devices also include patient monitoring devices that are capable of monitoring patient vital signs, e.g. cardiac rhythms, hemodynamic physiological parameters (e.g. blood pressure), respiratory parameter (e.g. respiratory rate, blood oxygen levels and/or saturation, end tidal carbon dioxide, etc.), blood glucose monitoring, body temperature monitoring, etc.

Example Controller

Figure 7:
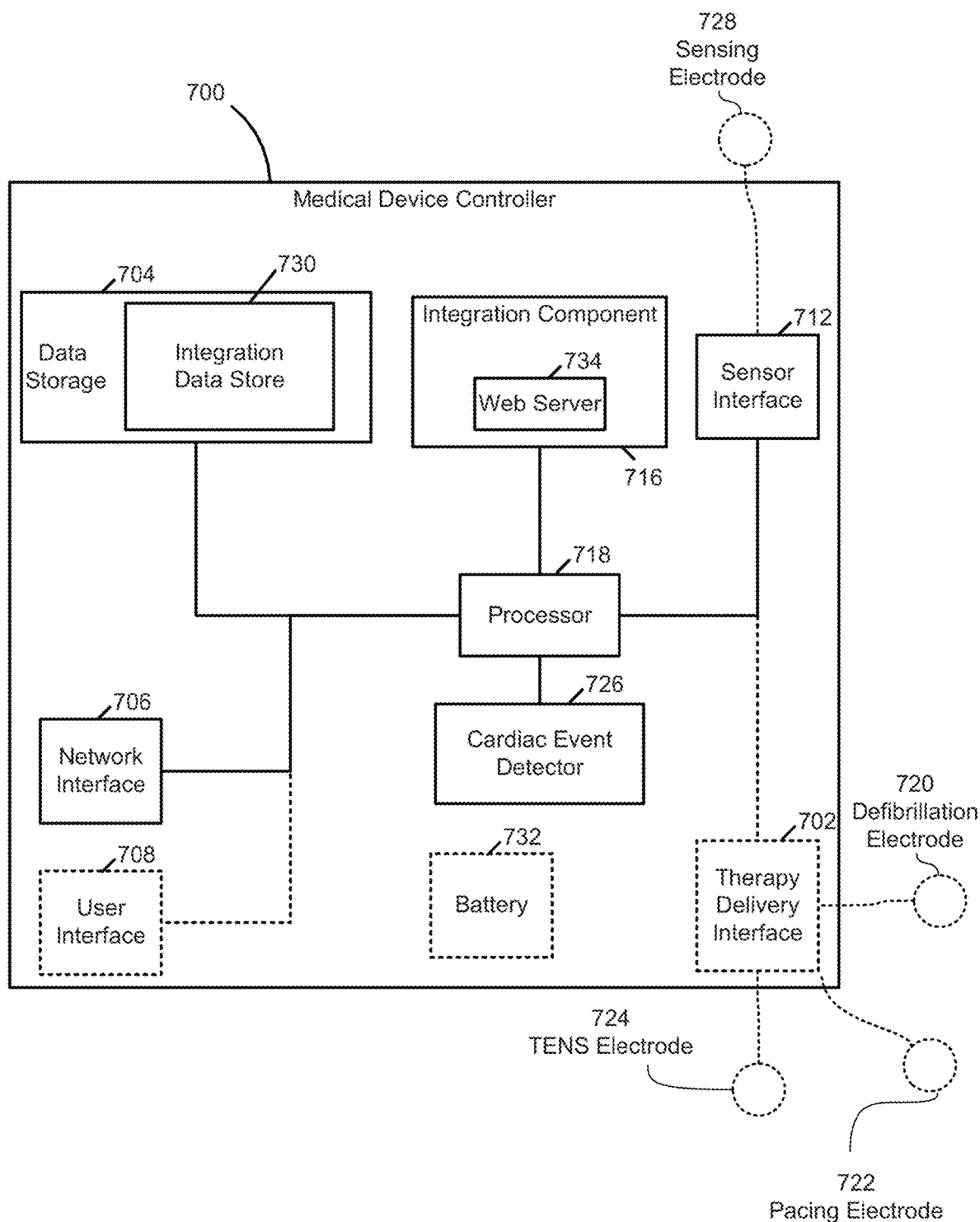
FIG. 7 is a schematic diagram of a medical device controller in accordance with an example of the present disclosure.

FIG. 7 shows a schematic of an example of a controller 700 that may be incorporated into the medical devices 102 and 104 according to some examples. For example, the controller 700 may be included within the medical device controller 520 illustrated in FIG. 5 and/or the housing of the monitor defibrillator 600. The controller 700 includes at least one processor 718, an integration component 716, a sensor interface 712, an optional therapy delivery interface 702, data storage 704 (which may include integration data store 730), a network interface 706, an optional user interface 708, and an optional battery 732. The sensor interface 712 may be coupled to any one or combination of sensors to receive patient data indicative of patient parameters. For example, the sensor interface 712 may be coupled to one or more sensing devices including, for example, sensing electrodes 728. The therapy delivery interface 702 (if included) may be coupled to one or more electrodes that provide therapy to the patient including, for example, one or more defibrillation electrodes 720, pacing electrodes 722, and/or TENS electrodes 724. In some examples, the sensing electrodes 728 are included in the sensing electrode 512 and the defibrillation electrode 720, the pacing electrode 722, and/or the TENS electrode 724 are included in the therapy electrodes 514. The sensor interface 712 and the therapy delivery interface 702 may implement a variety of coupling and communication techniques for facilitating the exchange of data between the sensors and/or therapy delivery devices and the controller 700.

In some examples, the network interface 706 can facilitate the communication of data between the controller 700 and one or more other devices or entities over a communications network, such as the network 112 described above with reference to FIG. 1. For example, where the controller 700 is included in an ambulatory medical device, the network interface 706 may be configured to communicate with a corresponding controller 700 included within a hospital medical device. In another example, the network interface 706 may be configured to communicate with the remote device 110 where a caregiver can access data related to the patient.

In some examples, the controller 700 includes a cardiac event detector 726 to monitor the cardiac activity of the patient, identify cardiac events experienced by the patient based on received cardiac signals, and treat the patient by executing a treatment sequence that culminates in the delivery of one or more defibrillating shocks to the body of the patient. The cardiac signals received by the cardiac event detector 726 may be acquired via electrodes integral to the medical device including the controller 700 or may be acquired by another medical device that is currently integrated with the medical device.

In some examples, the optional user interface 708 includes one or more physical interface devices such as input devices, output devices, and combination input/output devices and a software stack configured to drive operation of the devices. These user interface elements may render visual, audio, and/or tactile content, including content relating to location-specific processing. Thus the user interface 708 may receive input or provide output, thereby enabling a user to interact with the controller 700.

In some implementations, the processor 718 includes one or more processors that each are configured to perform a series of instructions that result in manipulated data and/or control the operation of the other components of the controller 700. In some implementations, when executing a specific software process as provided herein (e.g., FIGS. 8-11), the processor 718 is configured to make specific logic-based determinations based on input data received, and further capable of providing one or more outputs that can be used to control or otherwise inform subsequent processing to be carried out by the processor 718 and/or other processors or circuitry with which processor 718 is communicatively coupled. Thus, the processor 718 reacts to specific input stimulus in a specific way and generates a corresponding output based on that input stimulus. In this sense, the structure of processor 718 according to one example is defined by the flow charts shown in FIGS. 8-11. In some example cases, the processor 718 proceeds through a sequence of logical transitions in which various internal register states and/or other bit cell states internal or external to the processor 718 may be set to logic high or logic low. This specific sequence of logic transitions is determined by the state of electrical input signals to the processor 718 and a special-purpose structure is effectively assumed by the processor 718 when executing each software instruction of the software process shown in FIGS. 8-11. Specifically, those instructions anticipate the various stimuli to be received and change the implicated memory states accordingly. In this way, the processor 718 may generate and store or otherwise provide useful output signals. It is appreciated that the processor 718, during execution of a software process is capable of processing specific input signals and rendering specific output signals based on the one or more logic operations performed during execution of each software instruction. As referred to herein, the processor 718 is configured to execute a function where software is stored in a data store coupled to the processor 718 that is configured to cause the processor 718 to proceed through a sequence of various logic decisions that result in the function being executed.

Is some examples, the integration component 716 is executable by the processor 718 and is configured to execute any of a variety of integration processes, such as any of the integration processes described further below with reference to FIGS. 8-11. In some examples illustrated by FIG. 7, the integration component 716 includes a web server 734 configured to exchange data with other devices via the network interface 706.

In some examples, the integration component 716 includes a communication component that is configured in accordance with the communication component disclosed in U.S. Patent Application Publication No. 2016/0321400, titled CLINICAL DATA HANDOFF IN DEVICE MANAGEMENT AND DATA SHARING, published Nov. 3, 2016, which is hereby incorporated herein by reference in its entirety. Such a communication component may facilitate communication between a first medical device and a second medical device during a medical event. This communication may include transfer, display, and operational use of clinical data collected by the first medical device.

In some examples, the integration component 716 includes a shielding component that is configured in accordance with the shielding component disclosed in U.S. Patent Application Publication No. 2016/0321418, titled CUSTOMER- OR PATIENT-BASED SELECTIVE DATA ENCRYPTION IN MEDICAL DEVICE MANAGEMENT, published Nov. 3, 2016, which is hereby incorporated herein by reference in its entirety. In some examples, the shielding component increases the security of the secure communication sessions established by the integration component 716 by selectively shielding part data elements exchanged between the devices involved in the secure communications sessions.

In various implementations, the controller 700 implements an embedded operating system that supplies file system and networking support. In one example, the controller 700 includes software features that provide relational database functionality, touch screen display drivers, audio generation, BLUETOOTH wireless networking, BLU- ETOOTH Low Energy (BLE) Beacon technology, networking security and firewalling, and data encryption services.

Example Integration Processes

Figure 8:
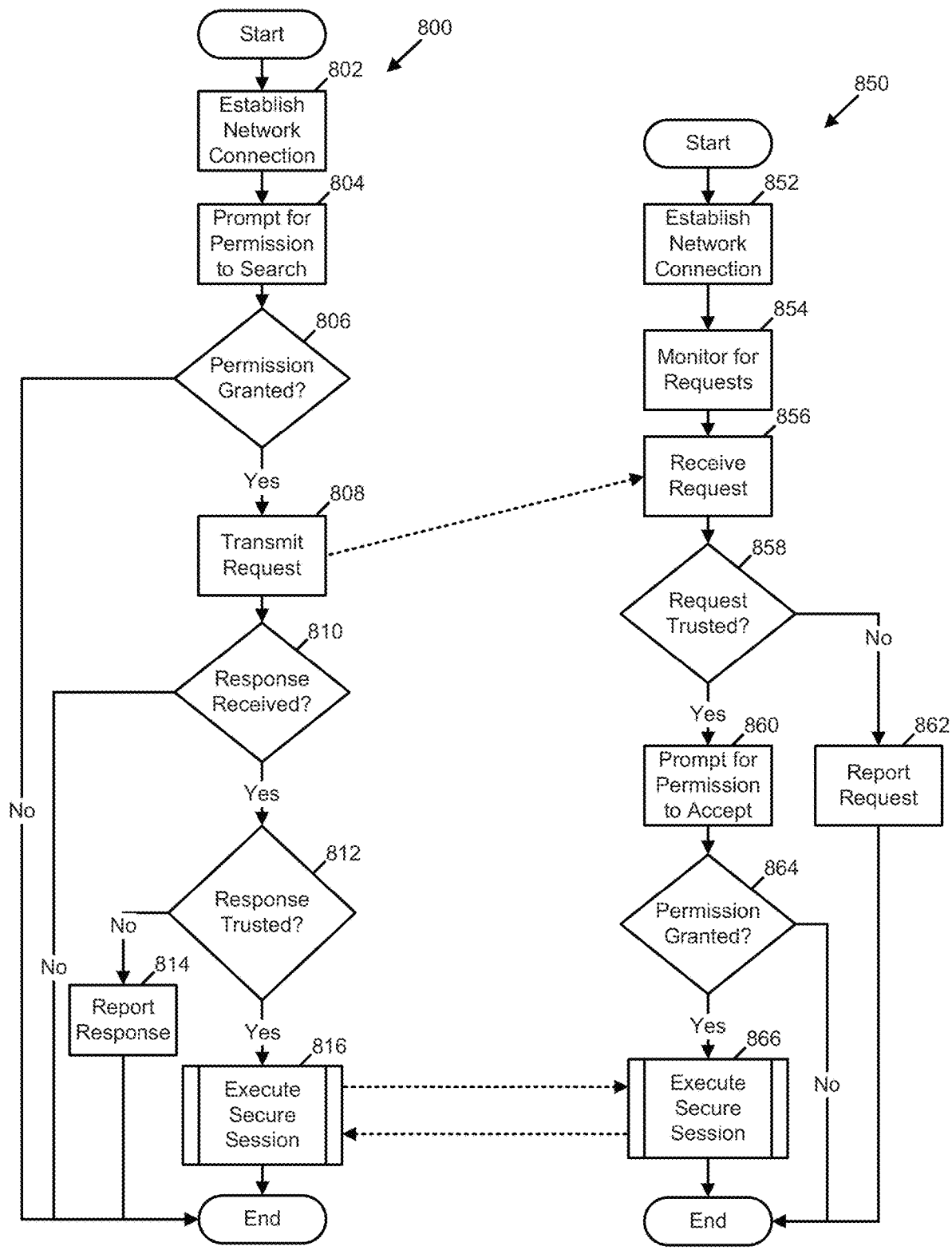
FIG. 8 is a flow diagram illustrating an integration process in accordance with an example of the present disclosure.

As described above, some example medical devices execute integration processes that establish and execute secure communication sessions with other medical devices in response to detecting that the other medical devices. FIG. 8 illustrates two corresponding integration processes in accordance with these examples. In some examples, each of two medical devices executing these integration processes include a controller (e.g., the controller 700) and an integration component (e.g., the integration component 716). In some implementations, the controller of the first of these medical devices (e.g., the ambulatory medical device 102) executes the integration process 800 and the controller of the second of these medical devices (e.g., the hospital medical device 104) executes the integration process 850. In other examples, the controller of a first medical device (e.g., the ambulatory medical device 102) executes the integration process 850 and the controller of a second medical device (e.g., the hospital medical device 104) executes the integration process 800. Further, in some examples, both of the controllers are configured to execute either integration process. Also, in some examples, other, non-medical devices (e.g., the remote device 110 and/or the programmable device 106) may execute either or both of the integration processes 800 and 850.

The integration process 800 starts in the act 802 with the first medical device establishing a network connection. This network connection may include a Wi-Fi connection, BLUETOOTH connection, near field communication connection, or any other connection through which programmable devices may exchange data. In act 804, the first medical device prompts a user (e.g., a patient or caregiver) for permission to search for trusted medical devices. In act 806, the first medical device determines whether the user granted permission. If not, the integration process 800 ends. Otherwise, the integration process 800 proceeds to act 808.

In the act 808, the first medical device transmits an integration request via the network connection. For example, in some embodiments, the first medical device may transmit a broadcast message encoded to a predefined format and including a digital certificate via the network connection. In act 810, the first medical device determines whether a response to the request is received within a timeout period. If not, the integration process 800 ends. Otherwise, the integration process 800 proceeds to act 812.

In the act 812, the first medical device determines whether the response is a trusted response. For example, the response may include a digital certificate authenticating the responding device as a trusted device. If the response is trusted, the integration process 800 proceeds to the act 816. Otherwise, the integration process 800 proceeds to the act 814.

In the act 814, the first medical device reports the untrusted response (e.g., to the user via the user interface, to another device via the network connection, etc.), and the integration process 800 ends. In the act 816, the first medical device executes a secure communication session with the second medical device, and the integration process 800 ends. Specific examples of processes executed during the act 816 are described further below with reference to FIGS. 9-11.

The integration process 850 starts in the act 852 with the second medical device establishing a network connection. This network connection may include a Wi-Fi connection, BLUETOOTH connection, near field communication connection, or any other connection through which programmable devices may exchange data. In act 854, the second medical device monitors the network connection for integration requests. In act 856, the second medical device receives an integration request. In act 858, the first medical device determines whether the request originated from a trust device. For example, the request may include a digital certificate authenticating the requesting device as a trusted device. If the request is trusted, the integration process 850 proceeds to the act 860. Otherwise, the integration process 800 proceeds to the act 862.

In the act 862, the second medical device reports the untrusted request (e.g., to the user via the user interface, to another device via the network connection, etc.), and the integration process 850 ends. In act 860, the second medical device prompts a user (e.g., a caregiver) for permission to execute a secure communication session. In act 864, the second medical device determines whether the user granted permission. If not, the integration process 850 ends. Otherwise, the integration process 850 proceeds to act 866.

In the act 866, the second medical device executes a secure communication session with the first medical device, and the integration process 850 ends. Specific examples of processes executed during the act 816 are described further below with reference to FIGS. 9-11.

Processes in accordance with the integration processes 800 and 850 enable medical devices to execute a variety of integrated functions within a secure environment, thereby enhancing patient care.

Figure 9:
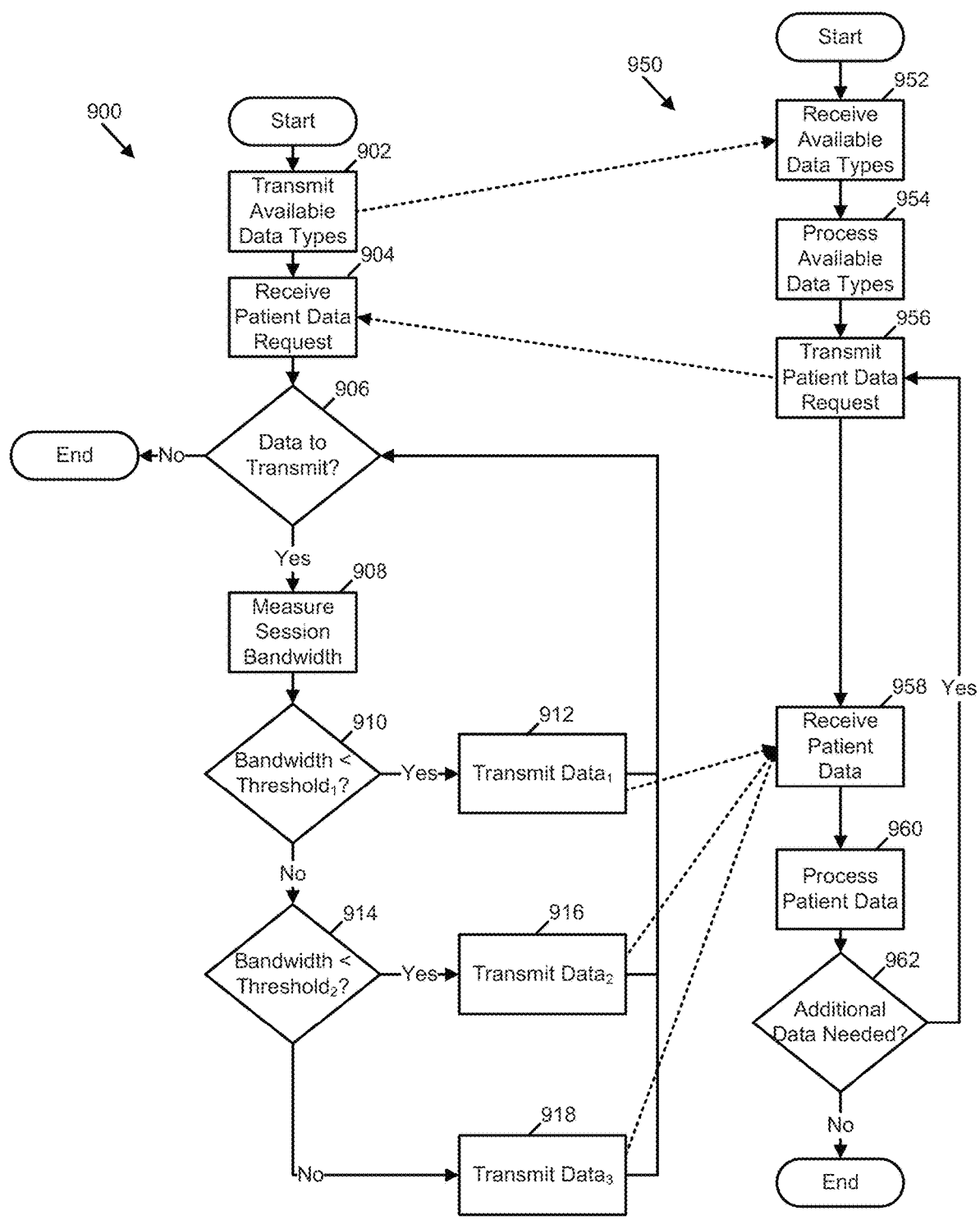
FIG. 9 is a flow diagram illustrating a patient data communication process in accordance with an example of the present disclosure.

As described above, some examples control the amount and type of data transferred between medical devices based on a data capacity measurement of a secure communication session between the medical devices. FIG. 9 illustrates two corresponding patient data communication processes 900 and 950 in accordance with these examples. In at least one of these examples, the patient data communication process 900 is executed within the act 816 by the first medical device, and the patient data communication process 950 is executed within the act 866 by the second medical (or non-medical) device.

The communication process 900 starts in act 902 with the first medical device transmitting an availability message to the second medical device. The availability message includes data descriptive of the types of detailed data and summary data the first medical device has available for transmission to the second medical device. In various examples, the types of detailed and summary data available may include any of the patient data described above.

The communication process 950 starts in act 952 with the second medical device receiving the availability message. In act 954, the second medical device processes the availability message. The processing may include parsing the availability message to identify the types of patient data available to the second medical device and selecting one or more patient data types for transmission. In some examples, the second medical device selects patient data types automatically according to default configuration data. In some examples, the second medical device presents a list of available patient data types to a caregiver via a user interface and selects patient data types that are designated by input received from the caregiver. In act 956, the second medical device transmits a patient data request to the first medical device. The patient data request may include identifiers of one or more requested patient data types.

In act 904, the first medical device receives and parses the patient data request. In act 906, the medical device determines whether patient data exists that is targeted for transmission to the second medical device. In various examples, patient data may be targeted for transmission by default (e.g., via configuration data stored in the first medical device) or by receipt of a patient data request. If patient data exists that is targeted for transmission to the second medical device, the communication process 900 proceeds to the act 908. Otherwise, the communication process 900 ends.

In act 908, the first medical device measures the data capacity of the secure communication session between it and the second medical device. For example, the first medical device may transmit a predefined, limited amount of data to the second medical device and extrapolate a data capacity measurement based on the amount of time to complete the transfer and the amount of data. In some examples, this limited amount of data is the availability message described above in the act 902.

In act 910, the first medical device determines whether the data capacity is less than a first threshold. If so, the first medical device transmits a first category of data in act 912 and returns to the act 906. The first category of data may require low data capacity to be successfully and timely transmitted. For example, the first category of data may be summary data descriptive of a patient (e.g., heart rate data). If the first medical device determines that the data capacity is not less than the first threshold, the communication process 900 proceeds to act 914.

In act 914, the first medical device determines whether the data capacity is less than a second threshold. If so, the first medical device transmits a second category of data in act 916 and returns to the act 906. The second category of data may require a moderate amount of data capacity to be successfully and timely transmitted. For example, the second category of data may be detailed data descriptive of the patient (e.g., ECG strip data). If the first medical device determines that the data capacity is not less than the second threshold, the communication process 900 proceeds to act 918.

In act 918, the first medical device transmits a third category of data and returns to the act 906. The third category of data may require a substantial amount of data capacity to be successfully and timely transmitted. For example, the third category of data may include both summary data descriptive of the patient and detailed data descriptive of the patient. In act 958, the second medical device receives the patient data. In act 960, the second medical device processes the patient data. This processing may include presenting the patient data to a caregiver and/or identifying (via input or automated processing) a need for additional patient data. Additional patient data may be needed, for example, where summary data is not precise enough to complete execution of the act 960. In act 962, the second medical device determines whether additional patient data is needed. If not, the communication process 950 ends. Otherwise, the second medical device returns to the act 956 and requests the additional patient data (e.g., detailed data corresponding to the summary data that was insufficient to complete execution of the act 960).

Processes in accord with the processes 900 and 950 enable medical devices to communicate data securely and effectively given any data capacity constraints present within the connection between them. While FIG. 9 illustrates two thresholds, other examples may employ greater or fewer thresholds without departing from the scope of the examples disclosed herein.

Figure 10:
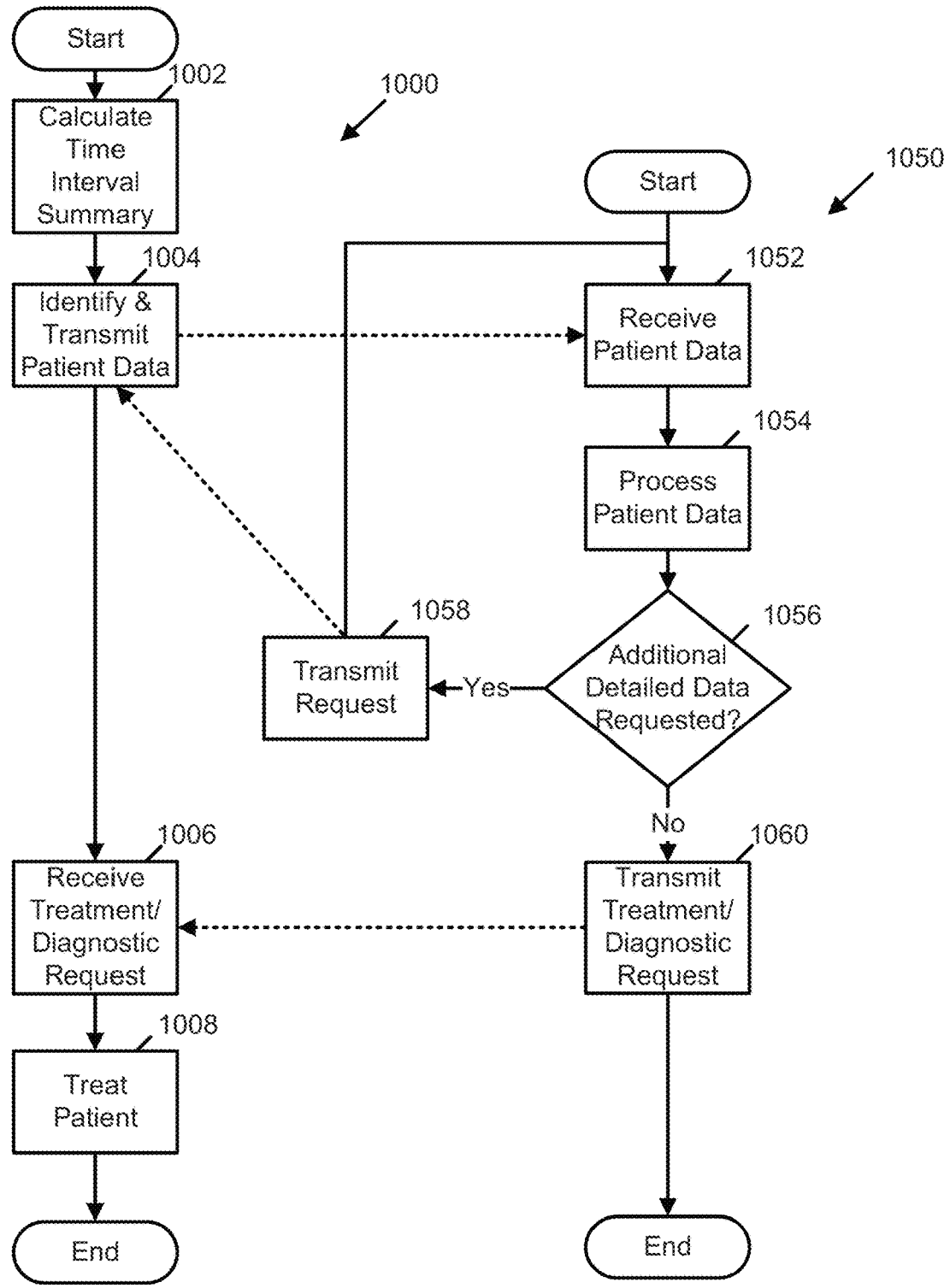
FIG. 10 is a flow diagram illustrating a medical device control process in accordance with an example of the present disclosure.

As described above, some examples enable devices to control operations of medical devices. FIG. 10 illustrates two corresponding secure control processes 1000 and 1050 in accordance with these examples. In at least some of these examples, the control process 1000 is executed within the act 816 by the first medical device, and the control process 1050 is executed in the act 866 by the second medical (or non-medical) device.

For example, the control process 1000 starts in the act 1002 with the first medical device calculating summary data by executing a predetermined summary process, e.g., a mobile cardiac telemetry process on detailed data acquired during one or more predetermined time intervals. For example, such time intervals may be a few minutes (e.g., in connection with a patient reported symptom and/or event), hours, days, weeks, or months. For example, the time interval may be specified via a predetermined user-configurable parameter. The summary data generated by such predetermined summary processing may include heartbeat identification, heart rate determinations, arrhythmia detections, etc. Summary data may further include, for example, information regarding the nature of an identified event, a time of occurrence of the event, and/or other information associated with the event, such as device configuration, patient data, and/or actions taken with regard to the information within the predetermined time interval. In act 1004, the first medical device identifies summary data and/or detail data to transmit to the second device as patient data and transmits the patient data to the second device. In some examples, the first medical device identifies the summary data and/or the detail data by processing a request for detailed data received via execution of the act 1056 as described further below. The request for detailed data may include an identifier of a time interval for which detail data is requested. In these examples, absent a specific request for detailed data, the first medical device may identify summary data and/or detailed data using a data capacity based process, such as the communication process described above with reference to FIG. 9.

The control process 1050 starts in the act 1052 with the second device receiving the patient data. In act 1054, the second device processes the patient data. Where the patient data received by the second device includes detailed data, the second device may, as part of the act 1054, execute processing to generate summary data from the detailed data, for example predetermined summary processing. Within the act 1054, the second device may also receive input from a caregiver via a user interface of the second device and incorporate and/or act upon data descriptive of the input. For example, the input may specify one or more portions of summary data for which detail data is requested.

For example, the second device is configured to take action based on one or more predetermined triggering events based on the received summary and/or detailed data. For instance, such a triggering event may be the indication of a treatable event as detected within the data stream from the first device. As an example, if the first device is an ambulatory medical device configured to treat the patient, the data from the first device may indicate a treatable condition, e.g., an onset of a cardiac arrhythmia such as Ventricular Fibrillation (VF) or Ventricular Tachycardia (VF). The second device is configured to alert a caregiver to the treatable condition as detected by the first device. For example, the alert provided via the second device may be in the form of one or more audible, tactile, visual, or other notification. The caregiver may review the alert and act on the alert by issuing a command via the user interface of the second device to the first device to initiate a treatment protocol. For example, the second device may instruct a wearable defibrillator to initiate a treatment protocol culminating in delivery of a therapeutic shock to the patient. In other examples, the treatment protocol can include initiation and/or monitoring of cardiac pacing pulses delivered to the patient by the first device.

In some examples, the first device can be configured to monitor one or more physiological parameters of the patient. For example, such a device may be a mobile cardiac telemetry (MCT) and/or a continuous event monitoring (CEM) device. An MCT/CEM device can be triggered, e.g., through the secure control processes described herein, to initiate a diagnostic protocol configured to monitor for certain patient conditions.

In some examples, the caregiver may cause the second device to initiate a request for additional data and/or detailed data from the first device prior to determining whether to initiate a treatment request to the first device.

In act 1056, the second device determines where additional and/or detailed data was requested within the act 1054. If so, the second device transmits a request for detailed data to the first medical device in act 1058. Otherwise, the second device executes the act 1060.

In act 1060, the second device transmits a treatment and/or diagnostic request generated by the act 1054, and the control process 1050 ends. The treatment and/or diagnostic request may request initiation or delay of treatment and/or a diagnostic protocol. In act 1006, the first medical device receives the treatment and/or diagnostic request (e.g., a request to deliver a defibrillating shock). In act 1008, the first medical device executes the treatment and/or diagnostic request (e.g., delivers a defibrillating shock), and the control process 1000 ends. A diagnostic request may request initiation or delay of a diagnostic protocol. For instance, in one example of the act 1006, the first medical device receives the diagnostic request (e.g., a request to initiate monitoring for a patient's heart rate transgressing one or more thresholds). In act 1008, the first medical device executes the diagnostic request (e.g., by adjusting one or more device and/or patient configuration parameters in response to the request).

Processes in accord with the control processes 1000 and 1050 enable medical devices to treat and/or monitor patients in view of a combination of physiological data acquired by two or more medical devices. In this way, these processes provide a caregiver with a variety of approaches to treating and/or monitoring a patient. For instance, execution of the control processes 1000 and 1050 may enable a caregiver to, for example, review patient data, such as ECG data, on a user interface of a monitor defibrillator even though the patient data is acquired by a distinct ambulatory medical device worn by the patient. Review of this patient data may enable the caregiver to control treatment, such as defibrillation and/or pacing, delivered by the ambulatory medical device and/or the monitor defibrillator via a single user interface of the monitor defibrillator. In other examples, execution of the control processes 1000 and 1050 may enable a caregiver to request and monitor a self-administered diagnostic protocol, such as a six-minute walk test.

Figure 11:
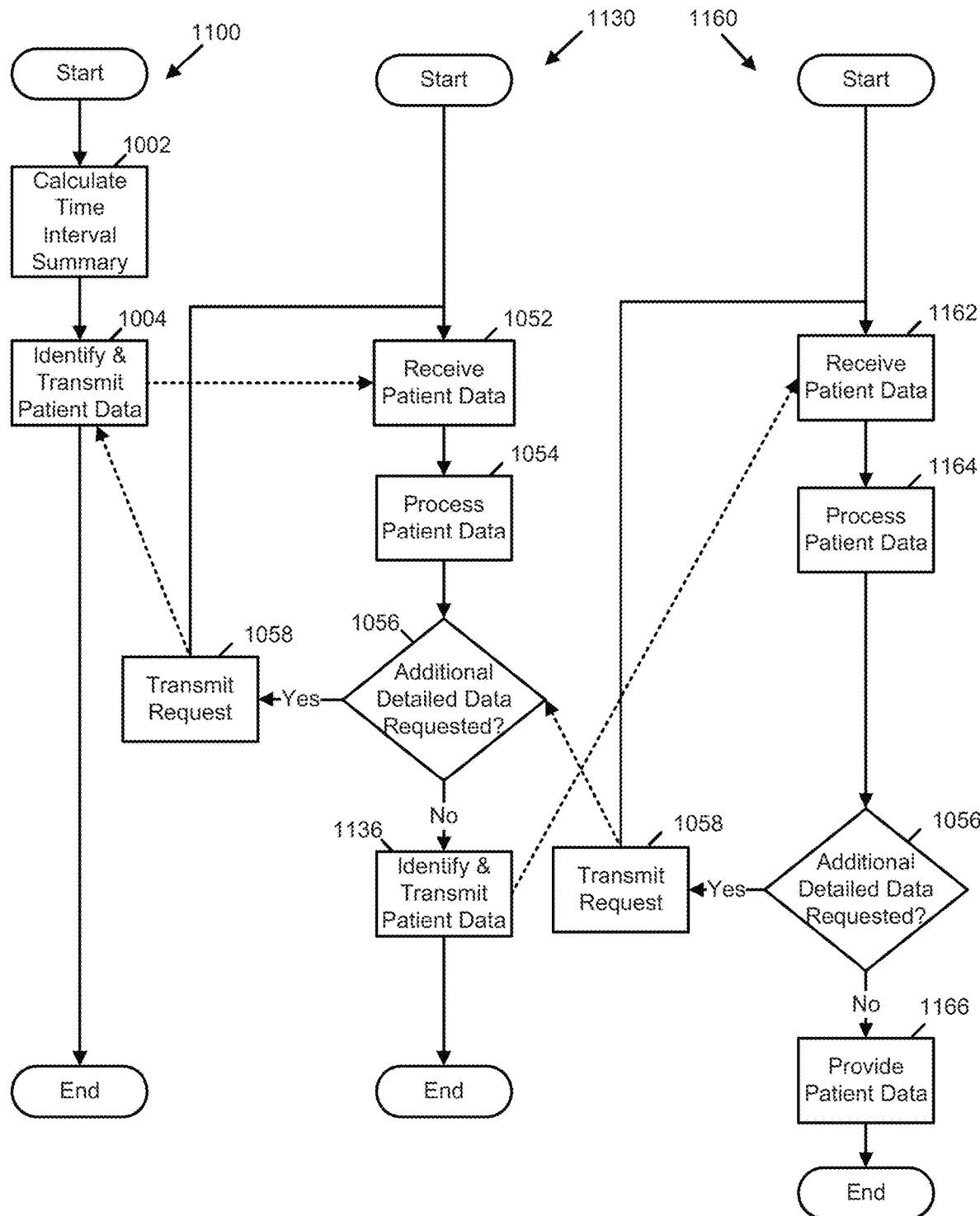
FIG. 11 is a flow diagram illustrating a patient data publication process in accordance with an example of the present disclosure.

As described above, some examples publish patient data from a medical device to other devices. FIG. 11 illustrates the corresponding patient data publication processes 1100, 1130, and 1160 in accordance with these examples. In some of these examples, the patient data publication process 1100 is executed within a first instance of the act 816 by the first medical device and the patient data publication process 1130 is executed within a first instance of the act 866 by the second medical device. Also, in some of these examples, the patient data publication process 1130 is executed within a second instance of the act 816 by the second medical device and the patient data publication process 1160 is executed by a non-medical device (e.g., the remote device 110 and/or the programmable device 106) within a second instance of the act 866.

The publication process 1100 starts with the first medical device calculating time internal summary data and transmitting patient data including the summary data to the second medical device by executing the acts 1002 and 1004 described above with reference to FIG. 10. The publication process 1130 starts with the second medical device receiving the patient data, processing the patient data, and selectively transmitting one or more requests for detailed data to the first medical device by executing the acts 1052, 1054, 1056, and 1058 described above with reference to FIG. 10. In act 1136, the second medical device transmits patient data including the summary data and the detailed data received and/or generated via execution of the acts 1052 and 1054 to the remote device.

The publication process 1160 starts in act 1162 with the remote device receiving the patient data. In act 1164, the remote device processes the patient data and the processed patient data. This processing may include parsing the data and creating a chronology of care that organizes patient summary data and patient detail data chronologically and identifies key handoff points during a patient overall treatment scenario. One example of a user interface presentation of a chronology of care is described below with reference to FIG. 13. Where the patient data received by the remote device in the act 1162 includes detailed data, the remote device may, as part of the act 1164, execute MCT processing to generate summary data from the detailed data. Within the act 1164, the remote device may also receiving input from a caregiver via a user interface of the remote device and incorporate and/or act upon data descriptive of the input. For example, the input may specify one or more portions of summary data for which detail data is requested. Next, the remote device selectively transmits one or more requests for detailed data to the second medical device by executing the acts 1056 and 1058 described above with reference to FIG. 10. In act 1166, the remote device provides the patient data, organized within a chronology of care, to a user or a device associated with a user and the publication processes 1100, 1130, and 1160 end.

Processes in accordance with the patient data publication processes 1100, 1130, and 1160 enable the efficient and secure distribution of data to disparately located medical devices. In this way, patients may benefit from caregivers both proximal to the patient and distant from the patient.

The processes disclosed herein each depict one particular sequence of acts in a particular example. The acts included in these processes may be performed by, or using, one or more programmable devices specially configured as discussed herein. Some acts are optional and, as such, may be omitted in accord with one or more examples. Additionally, the order of acts can be altered, or other acts can be added, without departing from the scope of the systems and methods discussed herein. Furthermore, as discussed above, in at least one example, the acts are performed on a particular, specially configured machine, namely a medical device configured according to the examples disclosed herein.

Example User Interfaces

Figure 12:
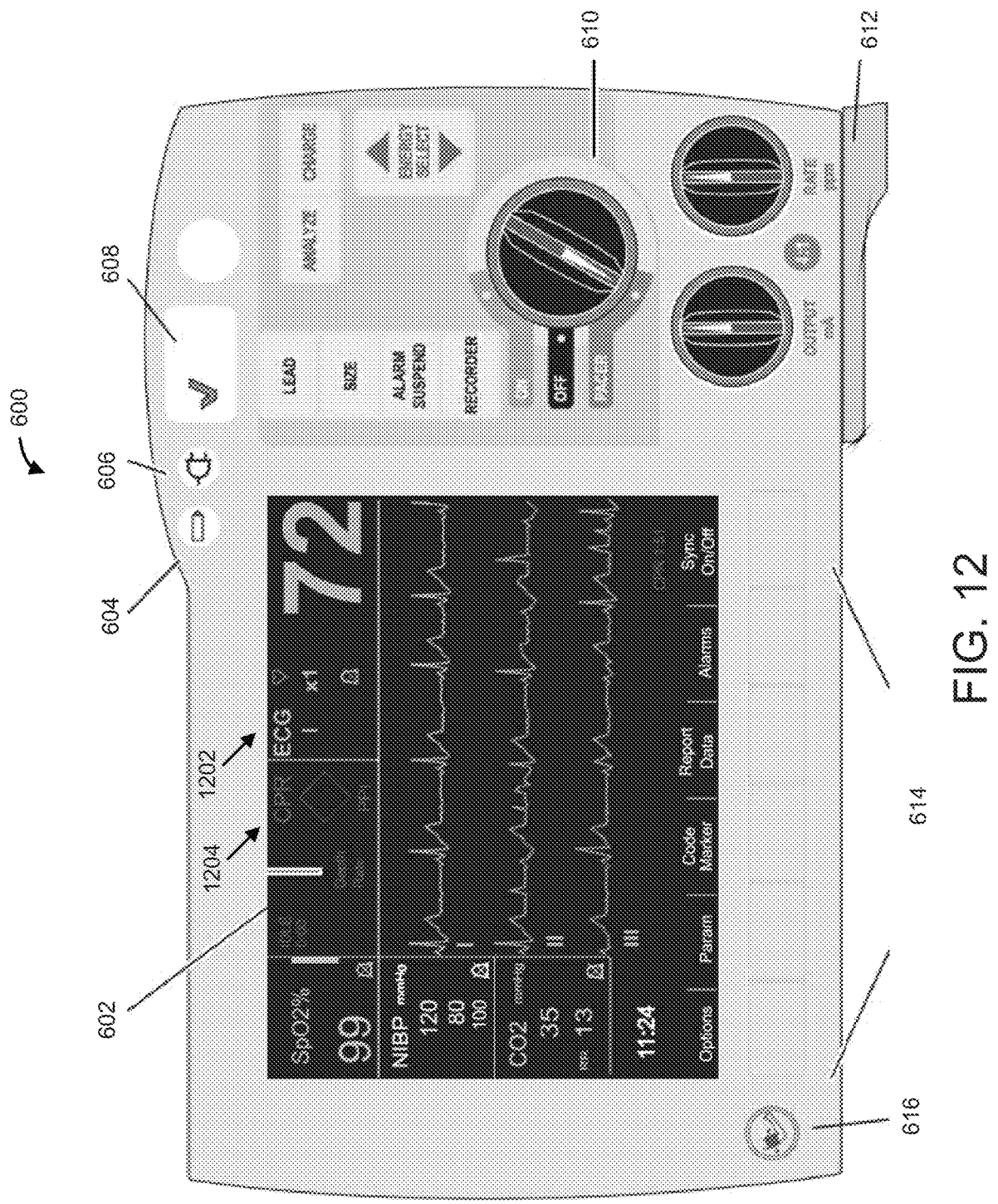
FIG. 12 is a schematic diagram of a user interface of a hospital medical device in accordance with an example of the present disclosure.

FIG. 12 illustrates an example monitor defibrillator 600 of FIG. 6 displaying user interface elements in accordance with some examples. As shown, the display screen 602 includes information derived from data generated by both the monitor defibrillator 600 and an ambulatory medical device (e.g., the ambulatory medical device 102). More particularly, in the example shown, elements 1202 and 1204 are based on data acquired by sensing electrodes and an accelerometer included in the ambulatory medical device and provide to the monitor defibrillator 600 in real time via the integration processes disclosed herein. In this way, the integrated system of medical devices is able to utilize the larger and more familiar (to hospital personnel) user interface of the monitor defibrillator to monitor and treat a patient without requiring that the patient be fitted with the electrodes physically integral to the monitor defibrillator.

Figure 13:
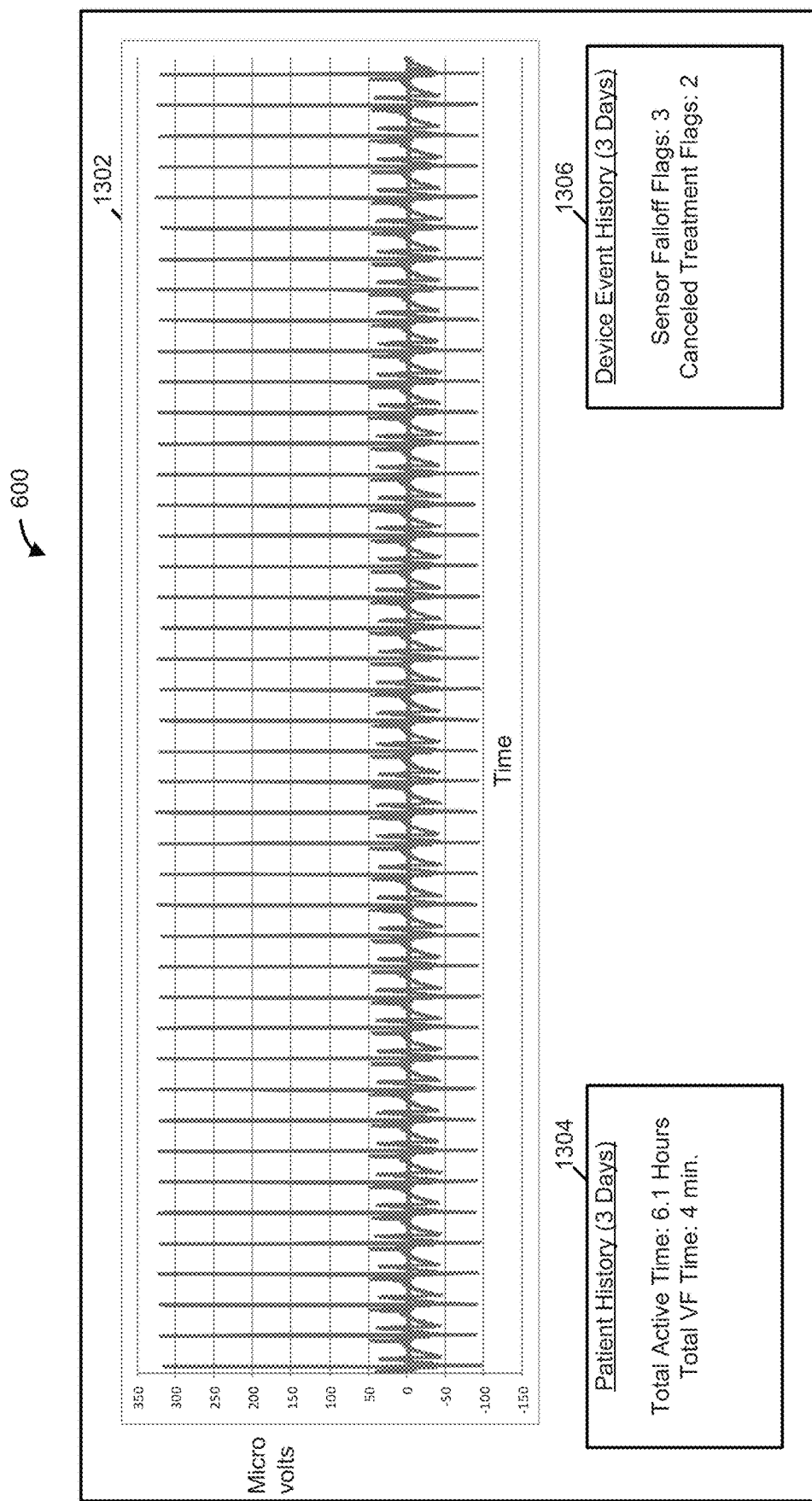
FIG. 13 is a schematic diagram of another user interface of a hospital medical device in accordance with an example of the present disclosure.

FIG. 13 illustrates another example monitor defibrillator 600 displaying information based on data received from a wearable defibrillator. In this example, the data includes ECG data 1302 recorded by the wearable defibrillator over a historical period (as shown, 3 days) while the patient wore the wearable defibrillator and conducted routine, daily activities. The monitor defibrillator 600 also displays a patient history 1304 and a device event history 1306. The patient history 1304 indicates the total amount of time the patient was active over the historical period (as shown, 6.1 hours) and the total amount of time the patient was experiencing ventricular fibrillation during the variable period (as shown, 4 minutes). The device event history 1306 displays the total number of flags the wearable defibrillator encountered during the historical period. The device history 1306 displays the number of sensor falloff flags (as shown, 3) and the number of canceled treatment flags (as shown, 2). As described above, the monitor defibrillator 600 may calculate this information from detailed data transmitted by the wearable defibrillator to the monitor defibrillator 600. Additionally or alternatively, the monitor defibrillator 600 may display summary data calculated and transmitted by the wearable defibrillator.

Figure 14:
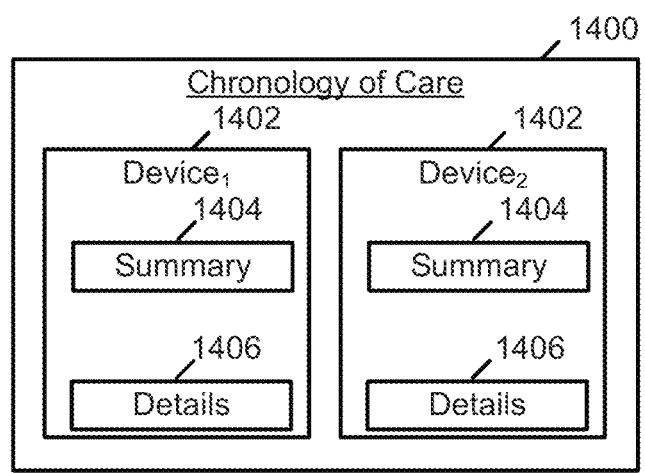
FIG. 14 is a schematic diagram of a chronology of care in accordance with an example of the present disclosure.

FIG. 14 illustrates a user interface presenting patient data within a chronology of care 1400 in accordance with some examples. As shown, the chronology of care displays sections 1402 for each medical device contributing patient data to the chronology. In the illustrated example, patient data from two distinct medical devices is presented. Each of the sections 1402 includes summary patient data 1404 and detail patient data 1406 generated by the corresponding device.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

The invention claimed is:

1. A hospital medical device comprising:
at least one network interface; and
at least one processor coupled to the at least one network interface and configured to
detect, via the at least one network interface, an external ambulatory medical device,
establish a secure communication session with the external ambulatory medical device via the at least one network interface, the secure communication session having a data capacity,
receive a category of patient data via the secure communication session, the category being based on the data capacity, and
process the patient data.

2. The hospital medical device of claim 1, wherein the category of the patient data is patient summary data and the at least one processor is configured to request, in response to processing the patient summary data, detailed data upon which the patient summary data is based from the external ambulatory medical device via the secure communication session.

3. The hospital medical device of claim 1, wherein the at least one processor is configured to transmit patient data to the external ambulatory medical device via the secure communication session.

4. The hospital medical device of claim 1, wherein the hospital medical device comprises at least one of a defibrillator, a temperature management system, a ventilator, a resuscitation system, or a telemetry system.

5. The hospital medical device of claim 2, wherein the patient summary data is based on electrocardiogram data.

6. The hospital medical device of claim 5, wherein the patient summary data describes a heart rate of a patient.

7. The hospital medical device of claim 1, wherein the at least one processor is configured to determine whether the external ambulatory medical device is within a predefined range of the hospital medical device based on at least one of a Wi-Fi signal strength, a BLUETOOTH signal strength, or a near field communication signal strength.

8. The hospital medical device of claim 1, wherein the at least one processor is configured to determine whether the external ambulatory medical device is within a predefined range based on physical contact between the hospital medical device and at least one of the external ambulatory medical device and a patient.

9. The hospital medical device of claim 1, further comprising a user interface coupled to the at least one processor, wherein the at least one processor is configured to receive input via the user interface, to generate instructions to treat a patient based on the input, and to transmit the instructions to the external ambulatory medical device.

10. The hospital medical device of claim 9, wherein the at least one processor is configured to implement a web server to transmit the instructions within the secure communication session.

11. The hospital medical device of claim 1, further comprising a user interface coupled to the at least one processor, wherein the at least one processor is configured to receive input via the user interface, to generate instructions to execute a diagnostic protocol based on the input, and to transmit the instructions to the external ambulatory medical device.

12. The hospital medical device of claim 11, wherein the diagnostic protocol includes a six-minute walk test.

13. The hospital medical device of claim 1, wherein the at least one processor is configured to implement a web server to transmit the patient data to a programmable device distinct from the hospital medical device and the external ambulatory medical device.

14. The hospital medical device of claim 13, wherein the programmable device comprises at least one of a mobile computing device, a remote server, or a hospital information system.

15. The hospital medical device of claim 14, wherein the patient data comprises compliance data.

16. The hospital medical device of claim 1, further comprising a user interface coupled to the at least one processor, wherein the at least one processor is configured to receive instructions from the external ambulatory medical device to issue an alert via the user interface regarding a patient condition.

17. The hospital medical device of claim 16, wherein the at least one processor is configured to display the patient data on the user interface.

18. The hospital medical device of claim 1, wherein the category of the patient data comprises one or more of patient summary data or patient detail data.

19. The hospital medical device of claim 1, wherein the at least one processor is configured to:
    determine whether the external ambulatory medical device is a trusted medical device; and
    execute the secure communication session upon determining that the external ambulatory medical device is the trusted medical device.

\* \* \* \* \*